United States Patent [19]

Usui et al.

[11] Patent Number: 5,369,275
[45] Date of Patent: Nov. 29, 1994

[54] APPARATUS FOR SOLID SURFACE ANALYSIS USING X-RAY SPECTROSCOPY

[75] Inventors: Toshio Usui; Yuji Aoki; Masayuki Kamei; Tadataka Morishita, all of Tokyo, Japan

[73] Assignees: International Superconductivity Technology Center; Fujikura Ltd., both of Tokyo; Showa Electric Wire & Cable Co., Ltd., Kawasaka, all of Japan

[21] Appl. No.: 911,740

[22] Filed: Jul. 10, 1992

[30] Foreign Application Priority Data

| | | | |
|---|---|---|---|
| Jul. 11, 1991 | [JP] | Japan | 3-197065 |
| Aug. 14, 1991 | [JP] | Japan | 3-228723 |
| Aug. 14, 1991 | [JP] | Japan | 3-228724 |

[51] Int. Cl.$^5$ ............................................. H01J 37/26
[52] U.S. Cl. ................................ 250/310; 250/305; 250/306; 250/397; 378/44
[58] Field of Search ............... 250/310, 306, 307, 311, 250/441.11, 442.11, 397, 305, 398; 378/44, 70, 71, 49, 82, 84, 85, 81

[56] References Cited

U.S. PATENT DOCUMENTS

| | | | |
|---|---|---|---|
| 3,751,661 | 8/1973 | Packer et al. | 250/308 |
| 3,861,199 | 1/1975 | Barkhoudarian | 250/310 |
| 3,864,570 | 2/1975 | Zingaro | 250/310 |
| 4,233,509 | 11/1980 | Tamura et al. | 250/310 |
| 4,382,183 | 5/1983 | Kimura | 250/310 |
| 4,724,320 | 2/1988 | Ino et al. | 250/310 |
| 4,764,945 | 8/1988 | Tadahiro | 378/44 |
| 4,894,541 | 1/1990 | Ono | 250/310 |
| 4,916,720 | 4/1990 | Yamamoto et al. | 378/44 |
| 5,093,573 | 3/1992 | Mikoshiba et al. | 250/310 |
| 5,193,104 | 3/1993 | Bastie et al. | 250/307 |

OTHER PUBLICATIONS

Japanese Journal of Applied Physics, vol. 30, No. 9B 15 Sep. 1991, Tokyo JP, pp. L1689–L1691, T. Usui et al.: "Novel chemical analysis for thin films: scanning electron microscopy & total-reflection-angle x-ray spectroscopy (SEM-TRAXS)—x-ray take off angle effect".

Japanese Journal of Applied Physics, vol. 24, No. 6, Jun. 1985, Tokyo JP pp. L387–L390, S. Hasegawa et al.: "Chemical analysis of surfaces by total-reflection-angle x-ray spectroscopy in RHEED experiments (RHEED-TRAXS)".

Journal of Vacuum Science and Technology: Part B, vol. B7, No. 4, Aug. 1989, New York US pp. 714–719, T. Isu et al. "In situ scanning microprobe reflection high-energy electro diffraction observation of GaAs surfaces during molecular-beam epitaxial growth".

Review of Scientific Instruments, vol. 60, No. 7, Jul. 1989, New York US pp. 2219–2222, Y. Hirai et al.: "Soft x-ray analysis system for reflection secondary electron, and fluorescence spectroscopy".

Journal of Applied Physics, vol. 69, No. 12, Jun. 1991, New York US, pp. 8420–8422, Y. C. Sasaki et al.: "Zn drops at a Si surface measured by the refracted x-ray fluorescence method".

Japanese Journal of Applied Physics, vol. 19, No. 8, Aug. 1980, Tokyo JP pp. 1451–1457, S. Ino et al.: "Chemical analysis of surface by fluorescent x-ray spectroscopy using RHEED-SSD method", p. 1452, section 2.

Japanese Journal of Applied Physics, vol. 24, No. 6, Jun. 1985, pp. 286–289.

Shuji Hasegawa, et al. Chemical Analysis of Surfaces by Total-Reflection-Angle X-Ray Spectroscopy in RHEED Experiments (RHEED-TRAXS).

*Primary Examiner*—Constantine Hannaher
*Assistant Examiner*—Kiet T. Nguyen
*Attorney, Agent, or Firm*—Oblon, Spivak, McClelland, Maier & Neustadt

[57] ABSTRACT

An apparatus for solid surface analysis capable of carrying out the X-ray fluorescence analysis of the sample surface according to the characteristic X-rays detected by the energy dispersive X-ray detector. The apparatus can also obtain an enlarged image of the sample surface according to the secondary electrons emitted from the excited sample surface detected by the electron detector. The apparatus can also carry out an X-ray diffraction analysis of the sample surface according to diffracted X-rays detected by the diffracted X-ray detector. The apparatus is also capable of attaching or detaching the energy dispersive X-ray detector easily by incorporating a connection room which can be put in a vacuum state independent of the vacuum chamber.

20 Claims, 24 Drawing Sheets

APPARATUS FOR SOLID SURFACE ANALYSIS USING X-RAY SPECTROSCOPY

BACKGROUND OF THE INVENTION

1. Field of the Invention

The present invention relates to an apparatus for analyzing a solid surface by using an X-ray spectroscopy.

2. Description of the Background Art

The field of a solid surface chemistry is a highly important field not only as a field of fundamental research but also as a field which is deeply related to the various industrially useful practical problems such as absorption, catalysis, corrosion, electrode reaction, friction, and electronic characteristics. For example, the catalysis is not only important as it is utilized in the majority of the processes used in the chemical industry, but also as it is considered indispensable in resolving the resource and energy problem and the environmental problem which are becoming the major concerns in recent years.

As a consequence, a large amount of empirical facts has been accumulated in this field over the past years. However, a truly effective means for checking the surface of the matters directly has not been available until recently, so that there has been a long history of estimating the properties of the surface of the matters according to the indirectly obtained information.

In recent years, however, due to the rapid development of various physical and chemical instruments, there is a strong trend to produce new materials and devices with improved functions by appropriately controlling the arrangement, chemical composition, electronic state, vibration state, and depth distribution of the atoms on the solid surface. For this reason, the measurement of the solid surface state is acquiring an increasing significance in recent years.

Presently, the most widely used type of an apparatus for solid surface analysis is a scanning electron microscope (SEM).

In a scanning electron microscope, the electron beam generated from an electron gun is sharply converged by a condenser lens and then irradiated onto a sample surface while performing a scanning operation using deflection coils, and the reflected electrons or secondary electrons emitted from the irradiated sample surface are collected by an electron detector and amplified, such that the amount of the collected electron can be indicated by modulating the luminance on the Braun tube display according to the collected electron beam.

Moreover, by synchronizing the scanning of the electron beam bundles on the sample surface with the scanning on the Braun tube display, it is also possible to obtain the enlarged image of the sample surface in terms of the reflected electron image or the secondary electron image on the Braun tube display.

In a case of observing the sample surface by using such a scanning electron microscope, the amount of the emitted electrons is affected not only by the crystalline orientation but also by the unevenness and the step shaped structure on the surface, so that the contrast of the image reflects all of these factors. Accordingly, it is possible to observe the sample surface in an undestroyed state, without spoiling the sample in terms of the grain size and shape of the crystalline grains, and the shape and distribution of the precipitated materials.

In such a scanning electron microscope, it is possible to achieve a surface resolution of less than 100 Å by narrowing the electron beam, but the emission region for the X-ray fluorescence is rather wide spread. The reason for this is considered to be the following.

Namely, for a sample in which a substrate B has a thin film H formed thereon, in a case of observing the sample by using the electron beam with high energy (20 KeV for example) for the scanning electron microscope, there is a penetration of the electron beam into the sample in the form shown in FIG. 1.

As shown in FIG. 1, the electrons in the scanning electron microscope penetrate through the thin film H and diffuse deeply into the substrate B in a form of a droplet, so that there has been a problem that the X-ray fluorescence is generated not only from the thin film H but also from the substrate B.

Consequently, in the case of carrying out the composition analysis using the X-ray fluorescence excited by the electron beam of the scanning electron microscope, there has conventionally been a problem that the thin film H thinner than the droplet-shaped electron diffusion region cannot be analyzed accurately. In particular, the droplet-shaped electron diffusion region normally has a depth of several $\mu$m, so that the analysis of the thin film having the thickness less than 0.1 $\mu$m (1000 Å) has been practically impossible.

In addition, the X-ray fluorescence from the thin film H and the X-ray fluorescence from the droplet-shaped region are mixedly observed, so that there has also been a problem that the S/N ratio (ratio of the amount of the X-ray fluorescence from the thin film with respect to the amount of the X-ray fluorescence from the droplet-shaped region) becomes poor.

On the other hand, in 1980, there has been a proposition by Professor Ino of the University of Tokyo and others, for the elementary analysis of the sample surface at a high sensitivity using the excitation of the characteristic X-rays of the atoms constituting the sample surface by the electron beam of the reflection high energy electron diffraction (RHEED) and the detection of the excited characteristic X-rays by an energy dispersive X-ray detector (EDX). This new surface analysis method is known as the total-reflection-angle X-ray spectroscopy (TRAXS).

In this method, the setting of the take-off angle of the characteristic X-rays emitted from the sample in the vicinity of the total reflection angle $\theta c$ (zero to several degrees) of the X-rays is known to be effective in improving the detection sensitivity for the sample surface elements, so that this method can be effectively utilized for the elementary analysis of the surface. In addition, it is also possible in this method to obtain the information on the atomic configuration on the surface. Furthermore, as this method is applicable to the film of various thickness sizes ranging from a very thin film having layers of only several atoms to a rather thick film, it is also possible in this method to obtain the information on the boundary of the matters.

Now, in the conventional apparatus for carrying out this total reflection angle X-ray spectroscopy method, a detailed structure for the attachment of the energy dispersive X-ray detector for detecting the characteristic X-rays has a configuration shown in FIG. 2.

In this configuration of FIG. 2, a rod shaped probe 112 is pierced through a side wall 111 of a vacuum chamber containing the sample therein, and attached on the side wall 111 by means of a flange 113.

On a tip of this probe 112 placed inside the vacuum chamber, there is provided a window section 107 formed by beryllium (Be) or organic thin film, and the probe 112 contains a semiconductor X-ray detector and FET inside this window section 107.

Also, on the base end side of the probe 112 located outside of the vacuum chamber, there is provided a pulse height analyzer 110. In addition, an L-shaped base end portion of the probe 112 is connected to a heat insulated tank 115 for storing the liquid nitrogen.

The interior of the probe 112 has a vacuum heat insulation structure to which the liquid nitrogen stored in the tank 115 is supplied in order to cool down the semiconductor X-ray detector contained inside the probe 112, so as to reduce the dark current in the semiconductor X-ray detector.

Now, the energy dispersive X-ray detector to be attached to the side wall of the vacuum chamber as shown in FIG. 2 is actually a very expensive device, so that it is preferable for the energy dispersive X-ray detector to be attached detachably such that it can be used in several vacuum chambers, rather than being fixedly attached to a single vacuum chamber.

Moreover, in the case where the energy dispersive X-ray detector is attached to the vacuum chamber directly, at a time of the replacement of the energy dispersive X-ray detector, it becomes necessary to release the vacuum state inside the vacuum chamber, so that the sample cannot be maintained in the vacuum state for an extended period of time, and a considerable amount of time is required for the operation to release the vacuum state.

For this reason, conventionally, the side wall of the vacuum chamber is equipped with a window section formed by beryllium, such that observation can be made by bringing the tip of the probe 112 face to face with the window section provided on the side wall of the vacuum chamber while the probe 112 and the tank 115 are supported outside of the vacuum chamber. With this configuration, the operation of the X-ray detection in several vacuum chambers can be effectively handled by using only one energy dispersive X-ray detector, while avoiding the above described disadvantages related to the release of the vacuum state of the vacuum chamber, and in addition there is an advantage that the handling of the X-ray detection device becomes easier as it can be located in the normal atmosphere.

However, such a conventional apparatus for carrying out this total-reflection-angle X-ray spectroscopy method has been associated with the following drawbacks.

First, there is a case in which it is necessary to form the film on the sample surface directly inside the vacuum chamber in order to carry out the X-ray fluorescence analysis of this film at a time of its formation or immediately after its formation. In such a case, there is a possibility for contaminating the window section 107 provided on a tip of the probe 112 with the film formation materials, and such a contamination of the window section 107 causes the excitation of the characteristic X-rays of the film formation materials during the analysis, so that the error can be introduced into the analysis data.

When such a situation occurs, it becomes necessary to replace the window section 107, but such a replacement of the window section 107 in turn requires the operation of disassembling the probe 112 having the vacuum heat insulation structure, so that considerable amounts of cost, time, and labor are required for the replacement of the window section 107.

Also, in the case where the probe 112 is to be located in the normal atmosphere outside the vacuum chamber, there is an air layer between the tip of the probe 112 and the window section provided on the side wall of the vacuum chamber inevitably, so that a part of the characteristic X-rays are absorbed by this air layer and consequently the detection efficiency is lowered. In particular, the characteristic X-rays having energy below 1.7 KeV are very easily absorbed by the air containing the oxygen, nitrogen, and argon, so that they are hardly detectable in this case. As a result, it is practically impossible in this case to detect the characteristic X-rays of the elements such as C, N, O, F, Na, Mg, and Al which have energy below 1.7 KeV.

SUMMARY OF THE INVENTION

It is therefore an object of the present invention to provide an apparatus for solid surface analysis capable of obtaining an enlarged image of the sample surface according to the secondary electrons from the sample surface excited by the electron beam, while carrying out the X-ray fluorescence analysis of the sample surface according to the characteristic X-rays.

It is another object of the present invention to provide an apparatus for solid surface analysis capable of obtaining an enlarged image of the sample surface according to the secondary electrons from the sample surface excited by the electron beam, and additionally obtaining a diffraction pattern according to the reflection electrons, while carrying out the X-ray fluorescence analysis of the sample surface according to the characteristic X-rays.

It is another object of the present invention to provide an apparatus for solid surface analysis capable of carrying out an X-ray diffraction analysis of the sample surface according to diffracted X-rays, while carrying out the X-ray fluorescence analysis of the sample surface according to the characteristic X-rays.

It is another object of the present invention to provide an apparatus for solid surface analysis capable of carrying out the X-ray fluorescence analysis of the sample surface according to the characteristic X-rays, in which the energy dispersive X-ray detector for detecting the characteristic X-rays can be attached or detached easily.

According to one aspect of the present invention there is provided an apparatus for solid surface analysis, comprising: a vacuum chamber means for containing a sample to be analyzed; electron gun means for irradiating electron beam onto a surface of the sample contained in the vacuum chamber means; energy dispersive X-ray detector means for detecting X-ray fluorescence emitted from the surface of the sample excited by the electron beam from the electron gun means; and electron detector means for detecting secondary electrons emitted from the surface of the sample excited by the electron beam from the electron gun means; and a connection means for connecting the energy dispersive X-ray detector means to the vacuum chamber means, having one end connected to the vacuum chamber means, another end capable of detachably attaching the energy dispersive X-ray detector means, and a vacuum pump for creating a vacuum state in an interior of the connection means without affecting a vacuum state inside the vacuum chamber means.

According to another aspect of the present invention there is provided an apparatus for solid surface analysis, comprising: a vacuum chamber means for containing a sample to be analyzed; X-ray generation means for irradiating X-rays onto a surface of the sample contained in the vacuum chamber means; energy dispersive X-ray detector means for detecting X-ray fluorescence emitted from the surface of the sample excited by the X-rays from the X-ray generation means; diffracted X-ray detector means for detecting the X-rays diffracted by the surface of the sample excited by the X-rays from the X-ray generation means; and a connection means for connecting the energy dispersive X-ray detector means to the vacuum chamber means, having one end connected to the vacuum chamber means, another end capable of detachably attaching the energy dispersive X-ray detector means, and a vacuum pump for creating a vacuum state in an interior of the connection means without affecting a vacuum state inside the vacuum chamber means.

According to another aspect of the present invention there is provided an apparatus for solid surface analysis, comprising: a vacuum chamber means for containing a sample to be analyzed; energy particle beam generation means for irradiating energy particle beams onto a surface of the sample contained in the vacuum chamber means; energy dispersive X-ray detector means for detecting X-ray fluorescence emitted from the surface of the sample excited by the energy particle beams from the energy particle beam generation means; and connection means for connecting the energy dispersive X-ray detector means to the vacuum chamber means, having one end connected to the vacuum chamber means, another end capable of detachably attaching the energy dispersive X-ray detector means, and a vacuum pump for putting an interior of the connection means in a vacuum state without affecting a vacuum state inside the vacuum chamber means.

Other features and advantages of the present invention will become apparent from the following description taken in conjunction with the accompanying drawings.

DETAILED DESCRIPTION OF THE PREFERRED EMBODIMENTS

Referring now to FIGS. 3 to 12, a first embodiment of an apparatus for solid surface analysis according to the present invention will be described in detail.

First, referring to FIG. 3 and FIG. 4, the essential parts of the apparatus of this first embodiment will be described schematically.

Figure 1:
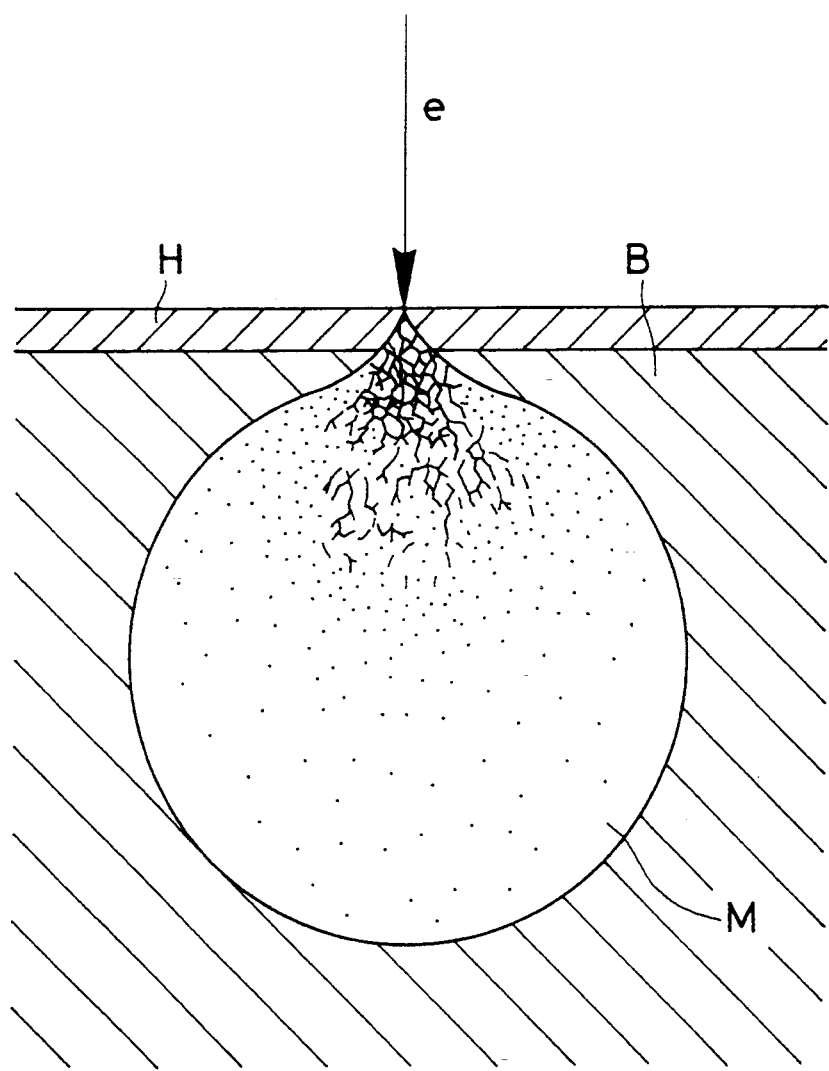
FIG. 1 is a cross sectional illustration showing a penetration of electron beam into a substrate member of a sample in a conventional scanning electron microscope.
Figure 2:
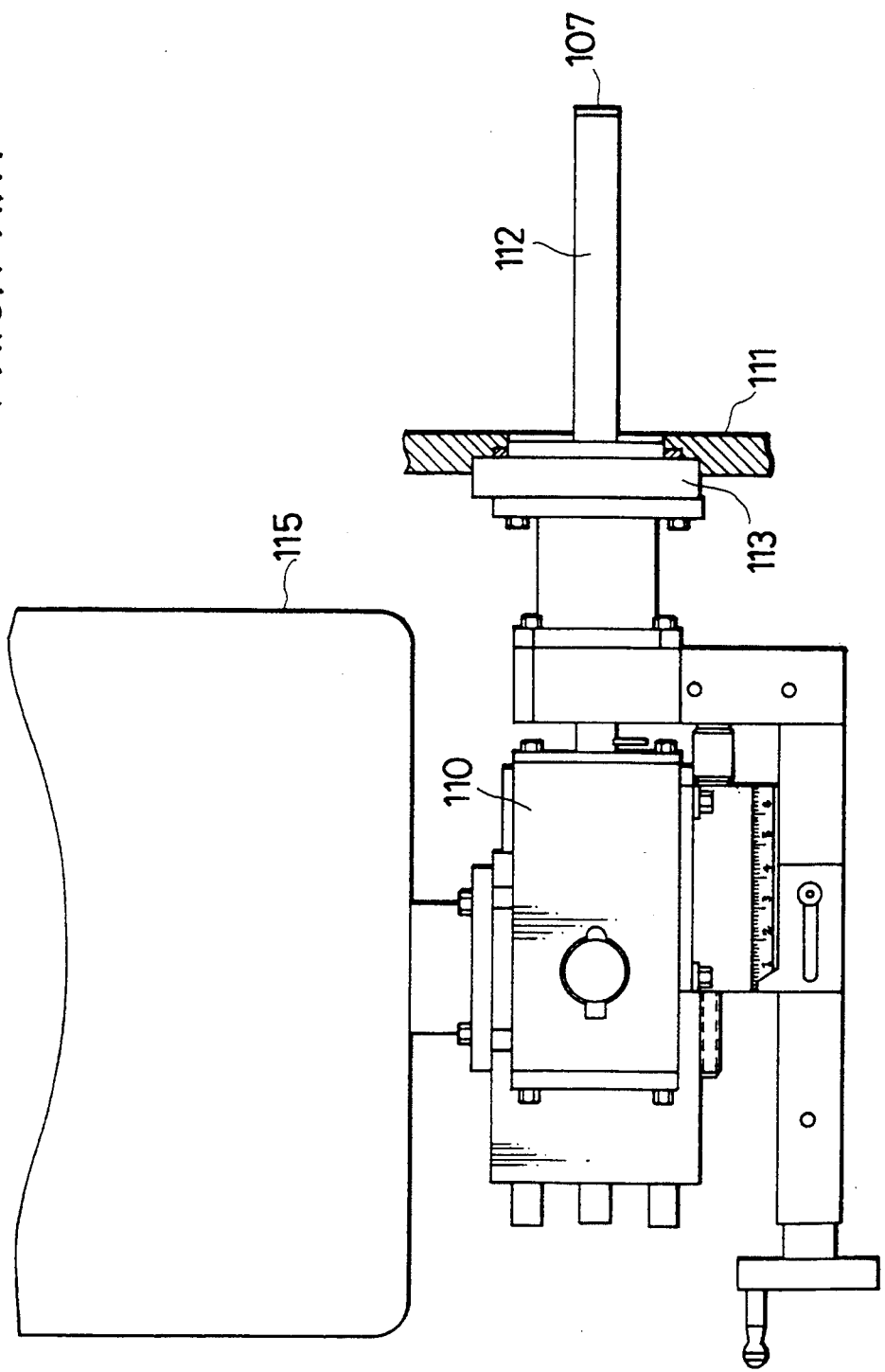
FIG. 2 is a longitudinal cross sectional view of a structure for attaching an energy dispersive X-ray detector to a side wall of a vacuum chamber in a conventional apparatus for solid surface analysis.
Figure 3:
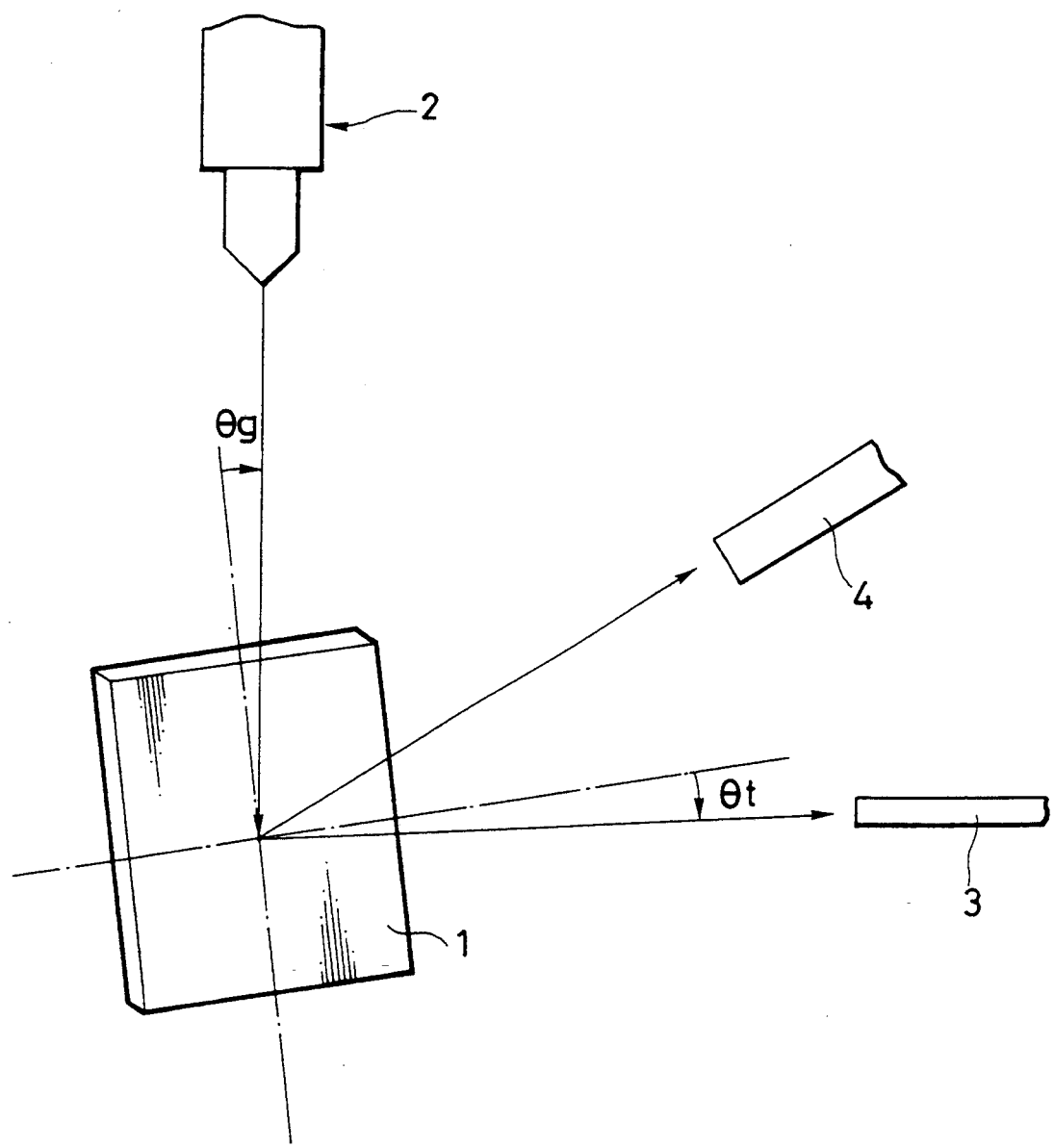
FIG. 3 is a schematic diagram indicating a conceptual configuration of a first embodiment of an apparatus for solid surface analysis according to the present invention.

As shown in FIG. 3, in this first embodiment, the apparatus includes an electron gun 2 for firing electron beam (energy particles) at an incident angle $\theta g$ onto a surface of a substrate shaped sample 1 on which a film to be analyzed is formed, an energy dispersive X-ray detector 3 for detecting X-ray fluorescence (characteristic X-rays) emitted from the surface of the sample 1 excited by the electron beam from the electron gun 2 at a take-off angle $\theta t$, and an electron detector 4 for detecting secondary electrons emitted from the surface of the sample 1 excited by the electron beam from the electron gun 2.

Figure 4:
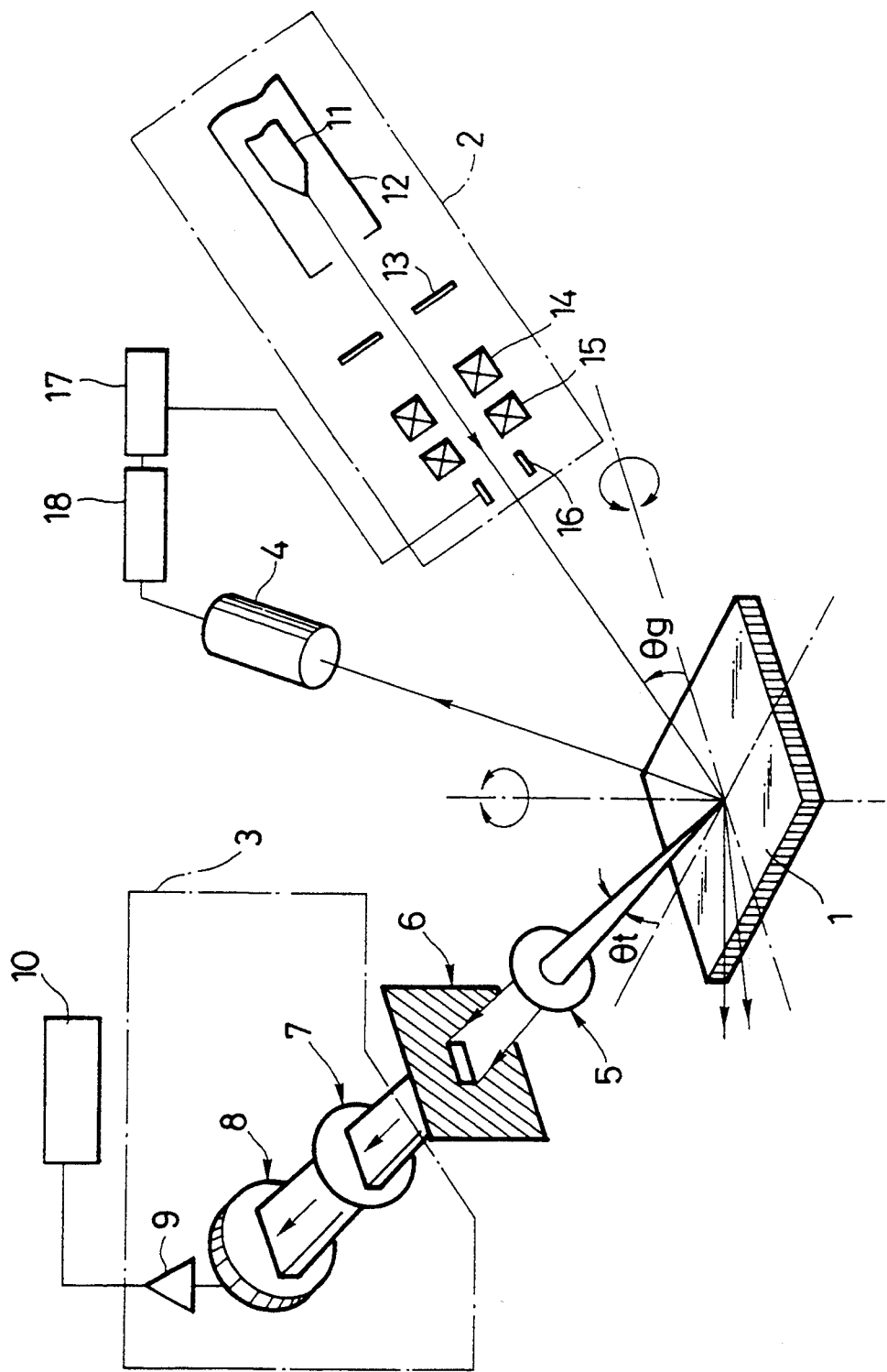
FIG. 4 is a schematic diagram showing a configuration of major components in the apparatus of the first embodiment in further detail.

In further detail, as shown in FIG. 4, the energy dispersive X-ray detector 3 is equipped with a window 5 and a slit 6 which are formed of beryllium or organic thin film which absorbs very little X-rays and are placed between the sample 1 and the energy dispersive X-ray detector 3. The energy dispersive X-ray detector 3 itself comprises a window section 7 formed by beryllium or organic thin film which absorbs very little X-rays, a semiconductor X-ray detector 8, and FET 9 connected to the semiconductor X-ray detector 8 as well as to an external pulse height analyzer 10 having an amplifier.

The energy dispersive X-ray detector (EDX) is a detector which indicates the intensity of the incoming X-rays in terms of electric signals by utilizing the fact that when the characteristic X-rays (or X-ray fluorescence) excited by the prescribed energy particles enter the detector, the production of a number of electron-hole pairs in proportion to the energy of the characteristic X-rays is caused in the detector.

The semiconductor X-ray detector 8 of this energy dispersive X-ray detector 3 is a so called Si(Li) semiconductor X-ray detector element which is formed by the thermal diffusion of Li in an p-type semiconductor single crystal of Si doped with B. When this semiconductor X-ray detector 8 is applied with the voltage and the X-rays enter this semiconductor X-ray detector 8, a number of electron-hole pairs in proportion to the energy of the entered X-rays are produced in the semiconductor X-ray detector 8, and these electron-hole pairs are collected by the positive and negative electrodes provided in the semiconductor X-ray detector 8, respectively, so as to be outputted in a form of a current pulse. With an appropriate amplification of such a current pulse output, it becomes possible to determine the energy of the entered X-rays according to the electrical signal level indicated by the output of the semiconductor X-ray detector 8. Here, it is to be noted the window 5 and the window section 7 are incorporated because of their high X-ray transmission efficiency.

On the other hand, as shown in FIG. 4, the electron gun 2 comprises a filament 11, Wehnelt cathode cylinder 12, anode 13, a first condenser lens 14, a second condenser lens 15, and a defection coil 16. This deflection coil 16 of the electron gun 2 is connected to a scanning electrode 17, while this scanning electrode 17 is connected to a monitoring Braun tube 18, and this monitoring Braun tube 18 is connected to the electron detector 4. Thus, this configuration is such that the electron beam can be irradiated from the electron gun 2 onto a desired position on the surface of the sample 1 by the function of the deflection coils 16, and the secondary electrons generated at the excited sample 1 can be received by the electron detector 4 such that the amount of the detected electrons can be indicated by modulating the luminance on the Braun tube 18 according to the detected electrons.

The solid surface analysis of the sample 1 can be carried out by using this apparatus of the first embodiment as follows.

First, the electron beam are incident from the electron gun 2 at the incident angle $\theta g$, which is in a range of 0 to 15 degrees and more preferably not greater than 4 degrees, onto the surface of the sample 1. As a result, the surface of the sample 1 is excited and the X-ray fluorescence (or characteristic X-rays) and the secondary electrons are emitted. The X-ray fluorescence is detected by the energy dispersive X-ray detector 3 at the take-off angle $\theta t$, which is in a range of zero to several degrees and more preferably not greater than 4 degrees, because the X-ray detection sensitivity is drastically improved at the total reflection angle of the X-rays, which is in a range of zero to several degrees and usually not greater than 4 degrees, so that the elementary analysis of the sample surface can be made while also obtaining the information on the atomic configuration on the sample surface. In addition, by detecting the secondary electrons by the electron detector 4, it is also possible to obtain the enlarged image of the sample at the same time.

Here, the total reflection angle $\theta c$ of the X-rays is known to be given by the following expression.

$$\theta c = 1.14 \times \rho^{0.5} \times E \text{ (deg)}$$

where $\rho$ (g/cm$^3$) is a density of the matter which reflects the X-rays, and E (KeV) is an energy of the X-rays. For example, the total reflection angle for the Y L$\alpha$ lines (having energy equal to 1.92 KeV) reflected by Au (having density equal to 19.3 g/cm$^3$) will be $\theta c$ (YL$\alpha$-Au)=2.60°. Similarly, the total reflection angle for the Au M lines (having energy equal to 2.15 KeV) reflected by Si (having density equal to 2.33 g/cm$^3$) will be $\theta c$ (AuM-Si)=0.81°. Thus, the total reflection angle of the X-rays varies according to the combination of the type of the X-rays to be measured and the material to reflect the X-rays, but it takes the value not greater than 4 degrees for the most of the cases.

Figure 5:
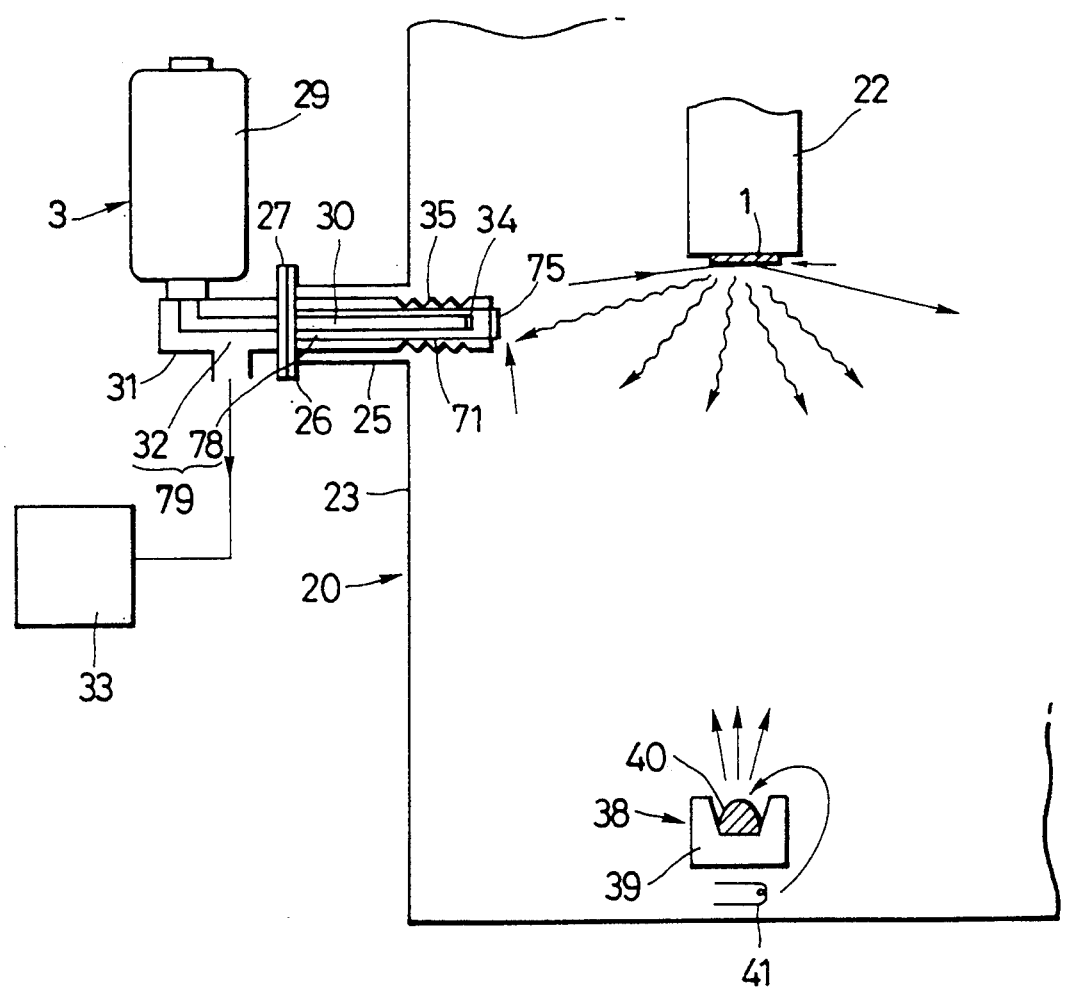
FIG. 5 is a schematic longitudinal cross sectional view of a structure for attaching an energy dispersive X-ray detector to a side wall of a vacuum chamber in the apparatus of the first embodiment.
Figure 6:
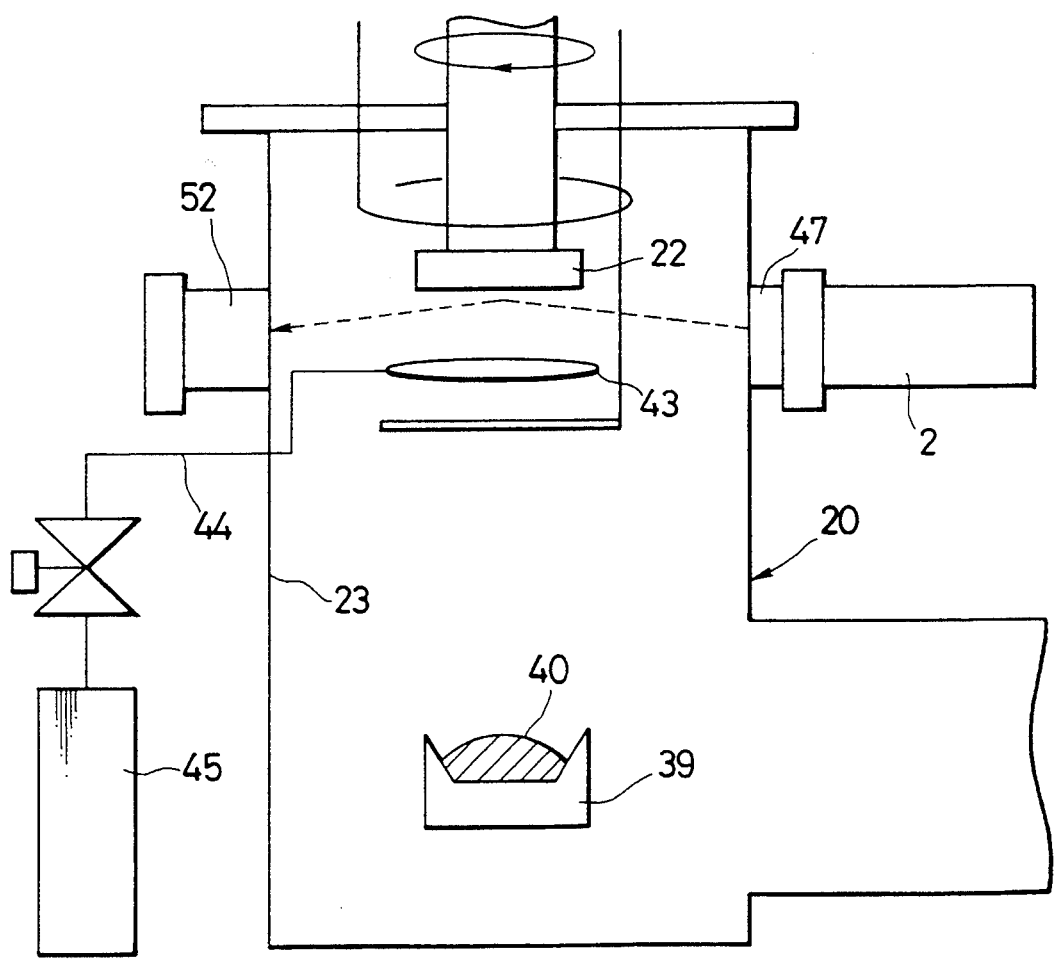
FIG. 6 is a schematic longitudinal cross sectional view of a vacuum chamber in the apparatus of the first embodiment.

Referring now to FIG. 5 and FIG. 6, more specific configuration of the major parts of the apparatus of this first embodiment will be described.

As shown in FIG. 5, the apparatus includes a vacuum chamber 20 for containing the sample 1, which is equipped with a vacuum pump (not shown) for producing the vacuum state inside the vacuum chamber 20. At an upper middle portion inside this vacuum chamber 20, there is provided a sample holder 22 for holding the substrate shaped sample 1 on its bottom face horizontally.

On a side wall 23 of the vacuum chamber 20, there is provided a cylindrical supporting port 25, to which the energy dispersive X-ray detector 3 is attached through a flange plate 26 provided at an opening end of the supporting port 25.

The energy dispersive X-ray detector 3 comprises a tank 29 for storing liquid nitrogen, an L-shaped probe 30 attached below the tank 29, an auxiliary tube 31 covering an outer face of a base end portion of the probe 30, and a flange plate 27 fixed at a front end of the auxiliary tube 31. The flange plate 27 is fixed with respect to the flange plate 26 on the supporting port 25 by bolts so as to form a spare room 32 connected to the supporting port 25 within the auxiliary tube 31. The auxiliary tube 31 is equipped with a vacuum pump 33 for producing a vacuum state inside the spare room 32.

The probe 30 has a window section 34 formed by beryllium or organic thin film at its tip end, and the semiconductor X-ray detector 8 and the FET 9 are contained inside the probe 30 behind this window section 34.

The supporting port 25 has cylindrical probe casing 35 formed by metal such as stainless steel, including a bellows section projecting inside the vacuum chamber 20, and inside the probe casing 35, there is provided a protection tube 71 for housing the probe 30, which has a window section 75 made of beryllium at its tip end.

Here, the space 78 formed between an inner wall of the protection tube 71 and an outer wall of the probe 30 is connected with the spare room 32 through the flange plates 26 and 27 such that this space 78 and the spare room 32 together form a connection room 79 to be put in the vacuum state by means of the vacuum pump 33 after the probe 30 is inserted into the protection tube 71.

On the other hand, at a bottom portion inside the vacuum chamber 20, there is provided a vacuum evaporation device 38 in which a raw material 40 is mounted on a crucible 39 and a deflected electron beam emission device 41 is provided below the crucible 39, such that the deflected electron beam emitted from the deflected electron beam emission device 41 can be irradiated onto the raw material 40 to evaporate the raw material 40, so that the desired film can be formed on the sample 1 by the evaporated raw material 40. This vacuum evaporation device 38 is utilized when it is necessary to apply the film formation process with respect to the sample 1 mounted on the bottom face of the sample holder 22.

On the other hand, as shown in FIG. 6, below the sample holder 22 inside the vacuum chamber 20, there is provided a gas supply device 43 formed by a ring shaped tube, which is connected to a gas supply source 45 such as an oxygen bottle located outside of the vacuum chamber 20 through a connection tube 44 provided through the side wall 23 of the vacuum chamber 20. The gas supply device 43 has a plurality of holes on the upper side of the ring shaped tube, such that the gas supplied from the gas supply source 45 can be supplied to a space below the sample holder 22.

In addition, as shown in FIG. 6, on one side of the side wall 23 of the vacuum chamber 20, there is provided an attachment port 47 to which the electron gun 2 is attached such that the electron beam from this electron gun 2 can be irradiated onto the sample 1 mounted on the bottom face of the sample holder 22.

Referring now to FIG. 7 to FIG. 12, a further detailed configuration of the apparatus of this first embodiment will be described.

Figure 7:
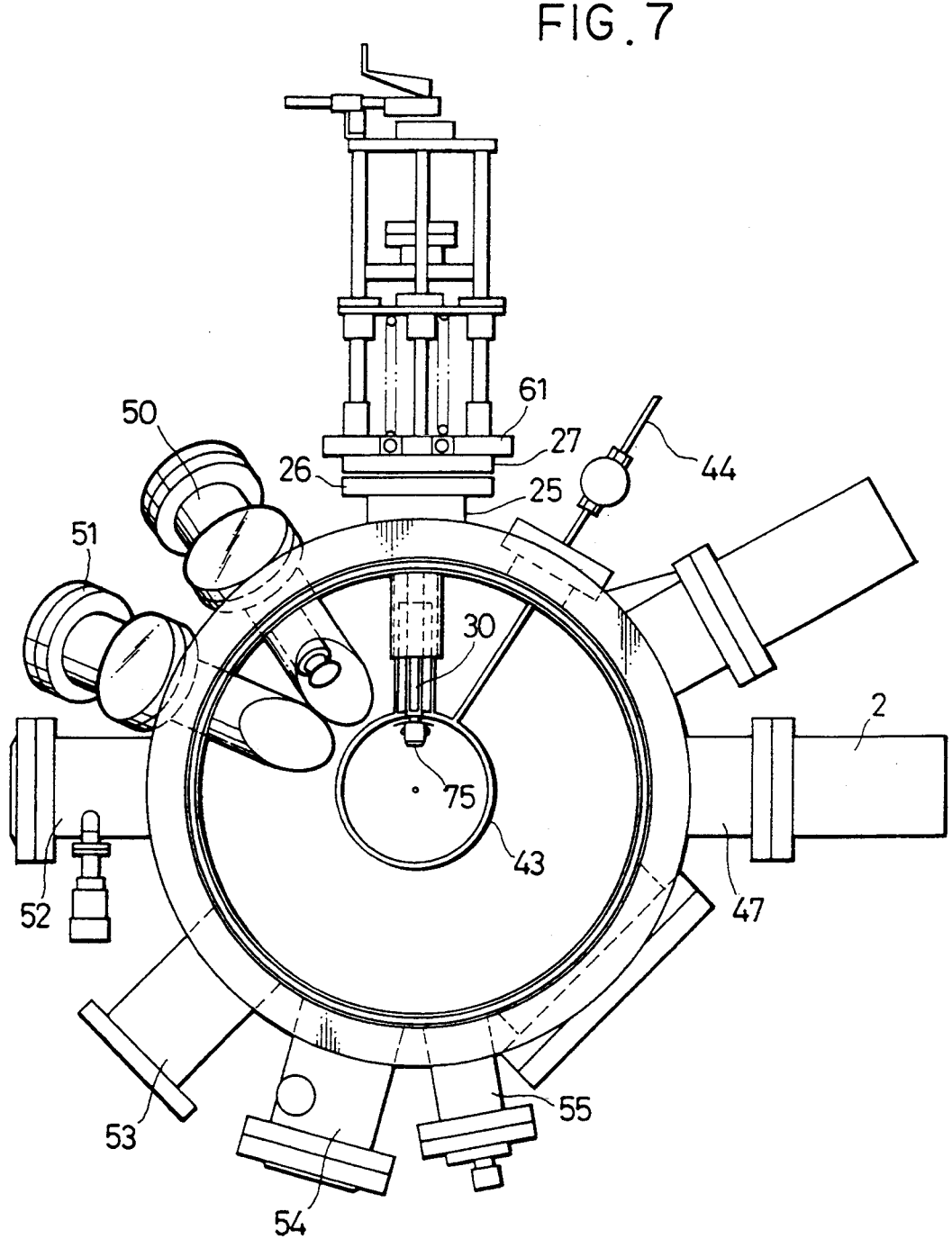
FIG. 7 is a transverse cross sectional view of the apparatus of the first embodiment.

In this embodiment, as shown in FIG. 7, the vacuum chamber 20 has a number of auxiliary ports 50, 51, 52, 53, 54, and 55 along its cylindrical side wall 23 in various directions, apart from the supporting port 25 and the attachment port 47, such that various instruments can be attached to the apparatus according to the need.

Figure 8:
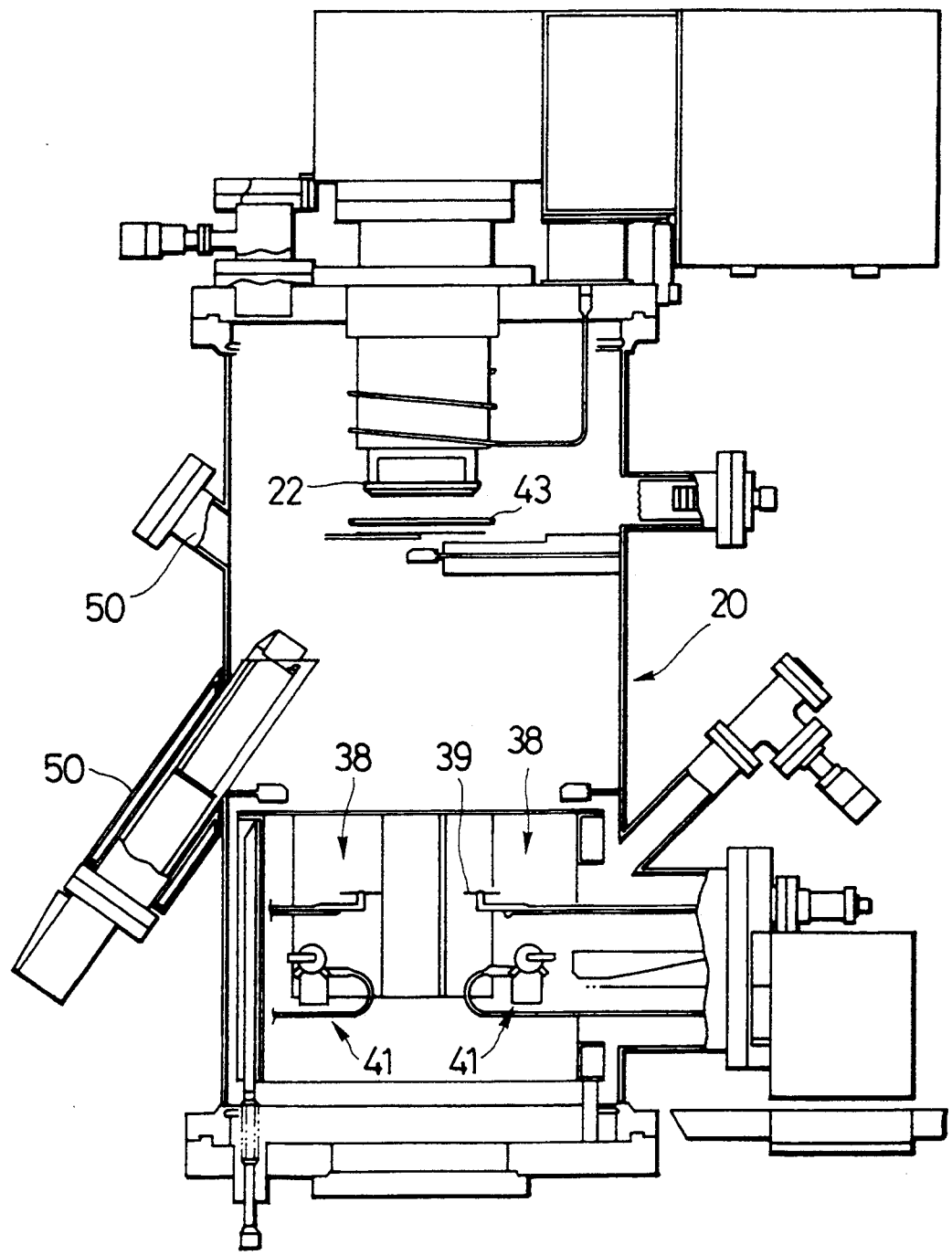
FIG. 8 is one longitudinal cross sectional view of the apparatus of the first embodiment.
Figure 9:
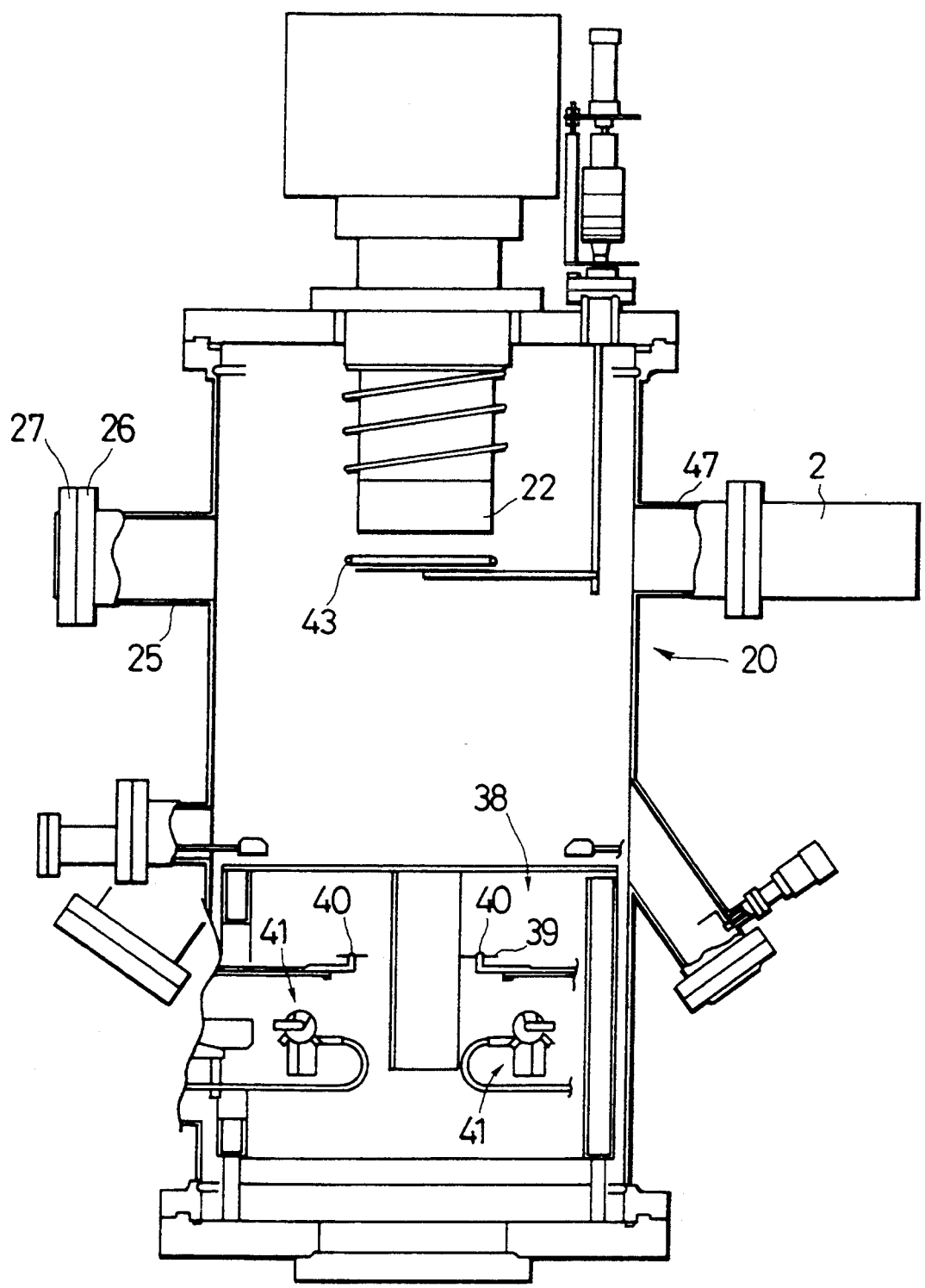
FIG. 9 is another longitudinal cross sectional view of the apparatus of the first embodiment.

The vacuum evaporation device 38 including the crucible 39 and the deflected electron beam emission device 41 actually has a configuration as shown in FIG. 8 and FIG. 9.

Figure 10:
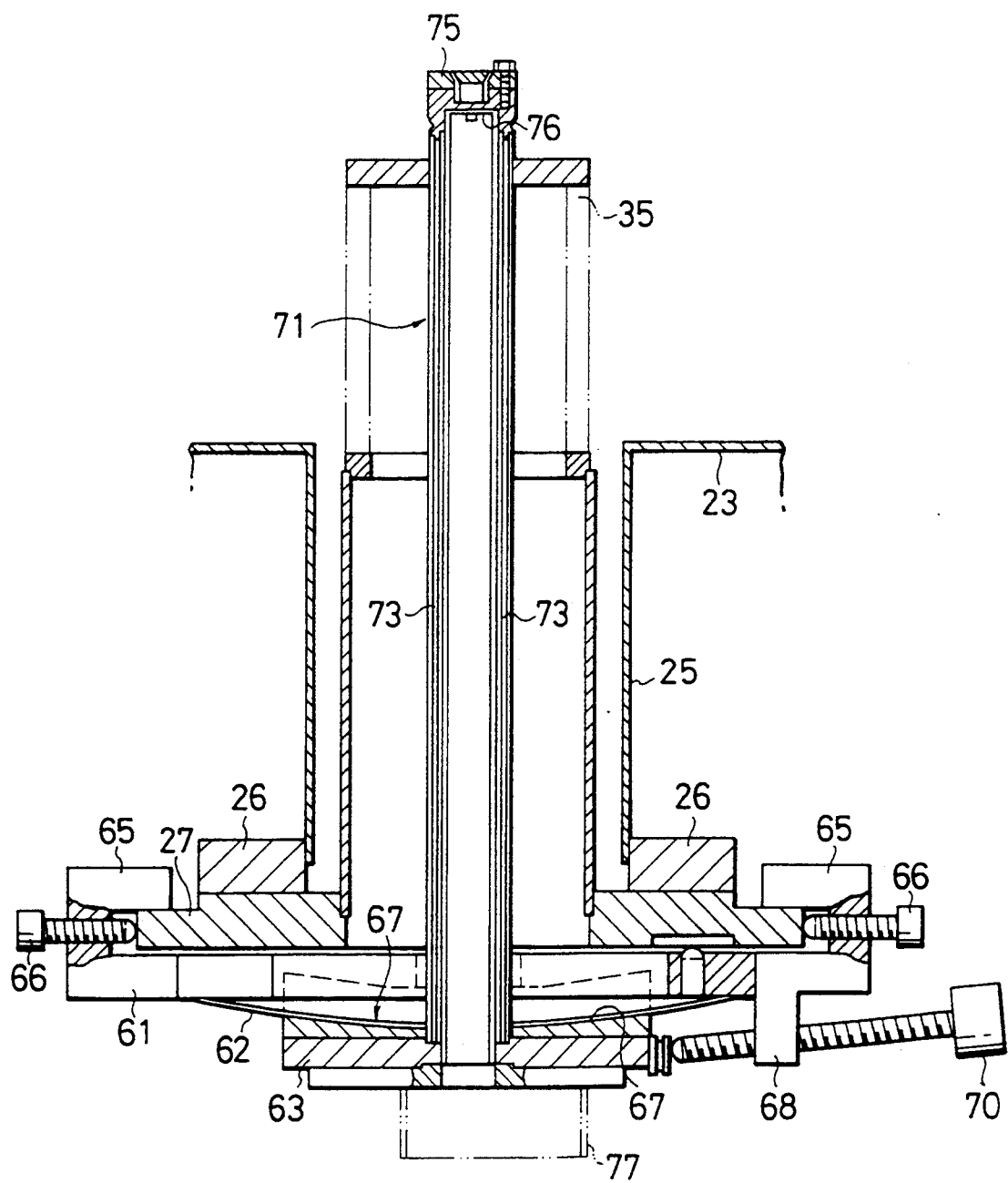
FIG. 10 is a detailed cross sectional view of the structure for attaching an energy dispersive X-ray detector schematically shown in FIG. 5 in the apparatus of the first embodiment.
Figure 11:
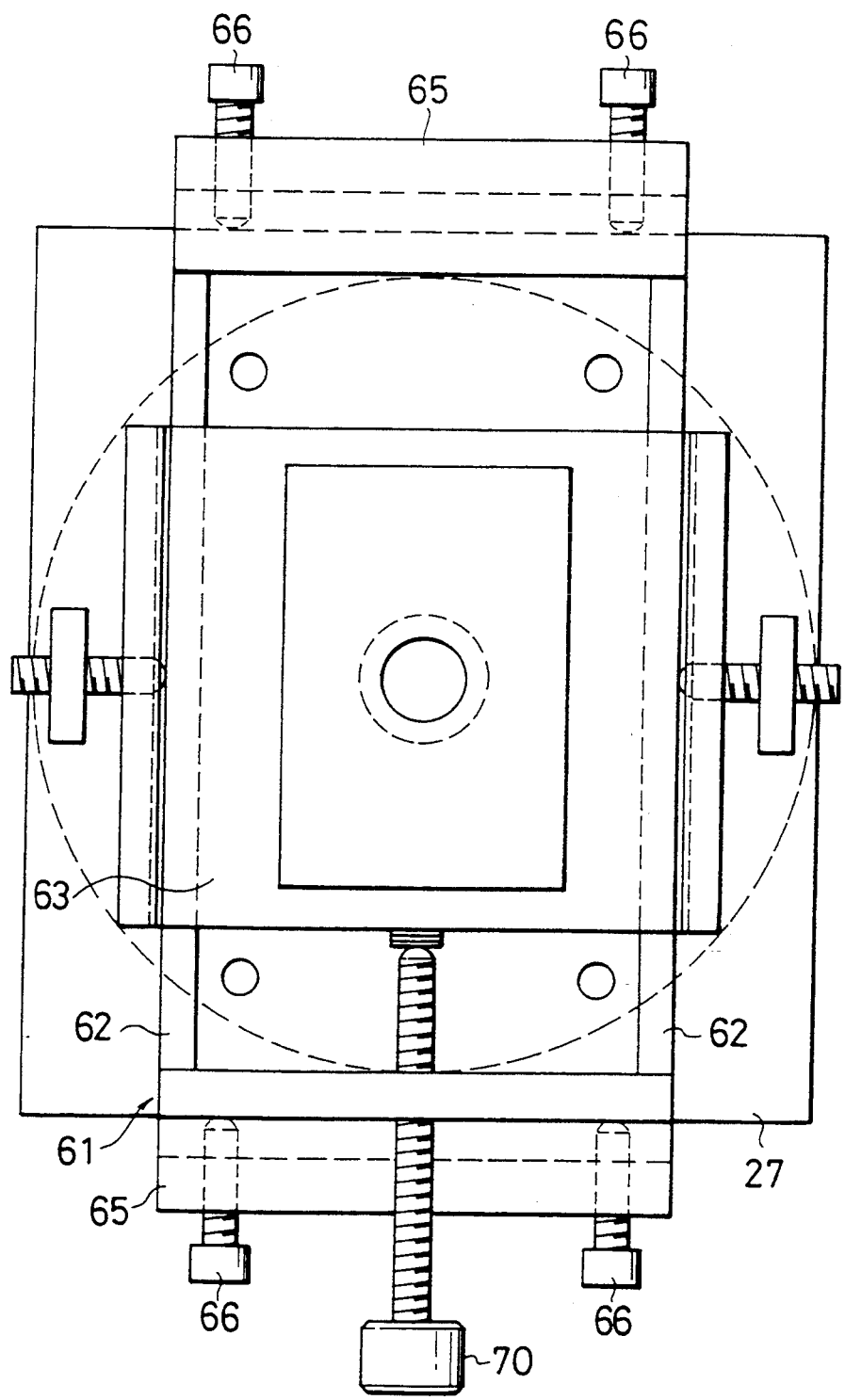
FIG. 11 is a detailed bottom view of the structure for attaching an energy dispersive X-ray detector schematically shown in FIG. 5 in the apparatus of the first embodiment.

The mechanism for supporting the probe 30 of the energy dispersive X-ray detector 3 has a detailed configuration as shown in FIG. 10 and FIG. 11.

Namely, the supporting port 25 of the vacuum chamber 20 has the flange plate 26 on inner side and the flange plate 27 on outer side, and the outer side of this flange plate 27 is attached with a slide frame 61 having a curved guide rails 62 for sliding a slide base 63 provided thereon on its outer side.

The slide frame 61 is attached to the flange plate 27 by means of clamping members 65 for clamping the edges of the flange plate 27, which are fixed with respect to the flange plate 27 by means of adjustment bolts 66 contacting with the side face of the flange plate 27 provided therethrough.

The slide base 63 has a guide face 67 in a concave shape corresponding to that of the guide rails 62 such that the guide base 63 can slide along the guide rails 62.

The slide frame 61 also has an extended portion 68 through which an adjustment bolt 70 contacting with the side face of the slide base 63 is provided.

The protection tube 71 projecting into the vacuum chamber 20 through the probe casing 35 pierces through the slide frame 61 and the slide base 63, and inside the window section 75 formed at a tip end of this protection tube 71, there is provided a slit 76. In addition, the protection tube 71 has a double casing structure incorporating a passage 73 for circulating the cooling water therethrough.

At the outer side of the slide base 63, there is provided a support frame 77 for mounting the base end portion of the energy dispersive X-ray detector 3 when the probe 30 is inserted into the protection tube 71.

Figure 12:
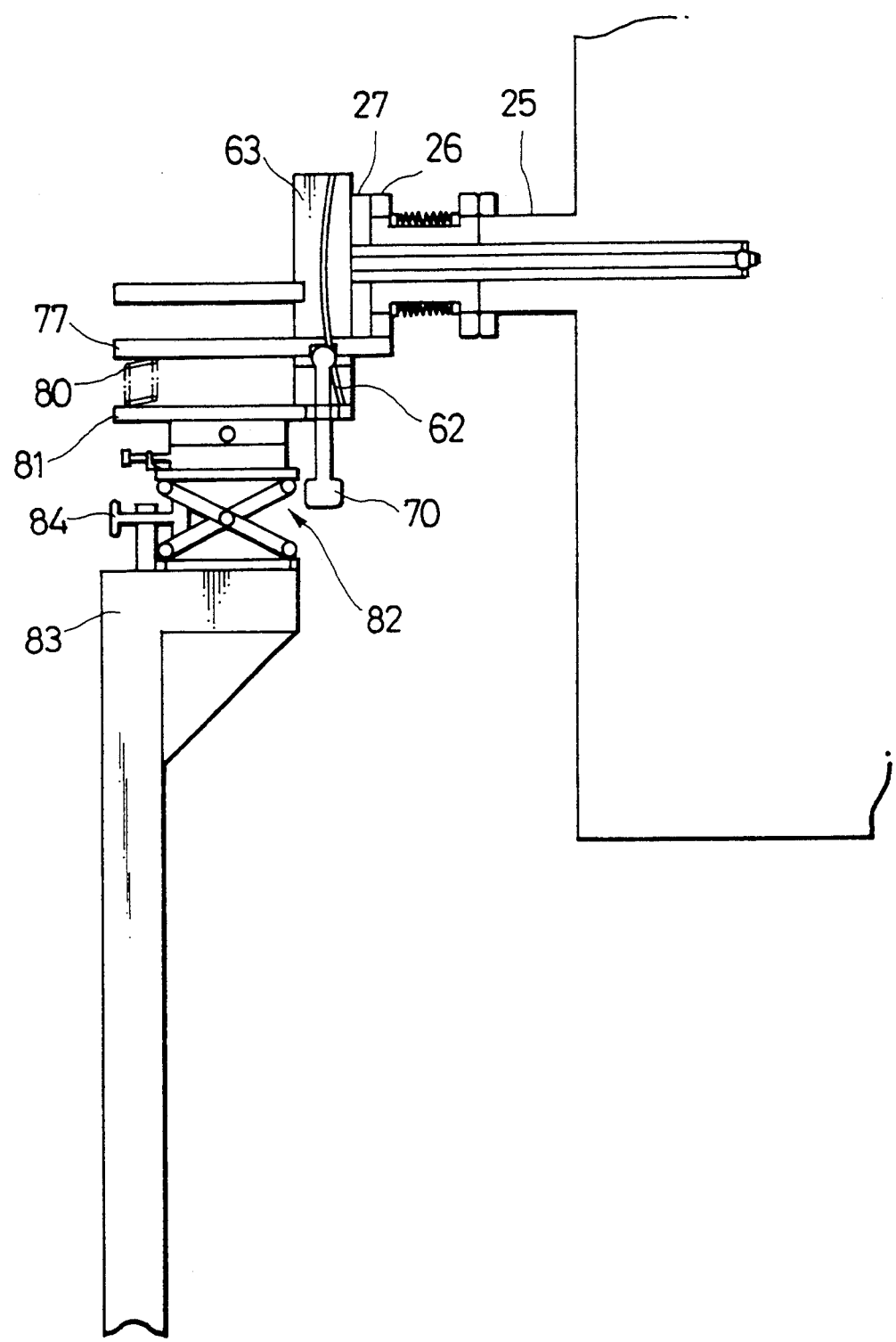
FIG. 12 is a detailed side view of the structure for attaching an energy dispersive X-ray detector schematically shown in FIG. 5 in the apparatus of the first embodiment.

Moreover, as shown in FIG. 12, the support frame 77 is supported on a moving frame 81 through a spring 80, and this moving frame 81 is supported on a base frame 83 through an X-shaped expansion lift mechanism 82 which is movable in a vertical direction by means of an adjustment bolt 84.

Now, the solid surface analysis operation of this apparatus of the first embodiment will be described in detail.

In carrying out the solid surface analysis of the sample 1 having a thin film H formed thereon, first, the sample 1 is mounted on the bottom face of the sample holder 22 inside the vacuum chamber 20, and then the vacuum chamber 20 is put in the vacuum state.

Meanwhile, the probe 30 of the energy dispersive X-ray detector 3 is inserted into the protection tube 71, and the energy dispersive X-ray detector 3 itself is mounted on the support frame 77. Then, the connection room 79 formed by the space 78 formed between an inner wall of the protect/on tube 71 and an outer wall of the probe 30 and the spare room 32 is put in the vacuum state by means of the vacuum pump 33.

In this state, the electron beam from the electron gun 2 is irradiated onto the surface of the sample 1 at the incident angle. This incident angle is preferably not greater than 4 degrees. The desirable value of this incident angle depends on the thickness of the thin film H formed on the sample surface, and with the smaller incident angle, it becomes possible to deal with the thinner film H because the penetration depth of the electrons can be reduced for the smaller incident angle.

The sample 1 irradiated by the electron beam has its surface excited such that the secondary electrons and the X-ray fluorescence are emitted from the sample surface. Here, as shown in FIG. 13, because of the smaller incident angle of the electron beam, the conventionally encountered droplet-shaped penetration of the electron beam into the substrate member B of the sample 1 does not occur in this embodiment, and only the thin film H is excited so that the secondary electrons and the X-ray fluorescence (characteristic X-rays) due to the components of the thin film H are emitted from the sample surface.

At this point, the electron beam is deflected by appropriately controlling the deflection coil 16 by the scanning electrode 17, such that the secondary electrons from the sample surface are detected by the electron detector 4 and consequently the enlarged image of the sample surface is displayed on the Braun tube 18, just as in the conventional scanning electron microscope.

Figure 13:
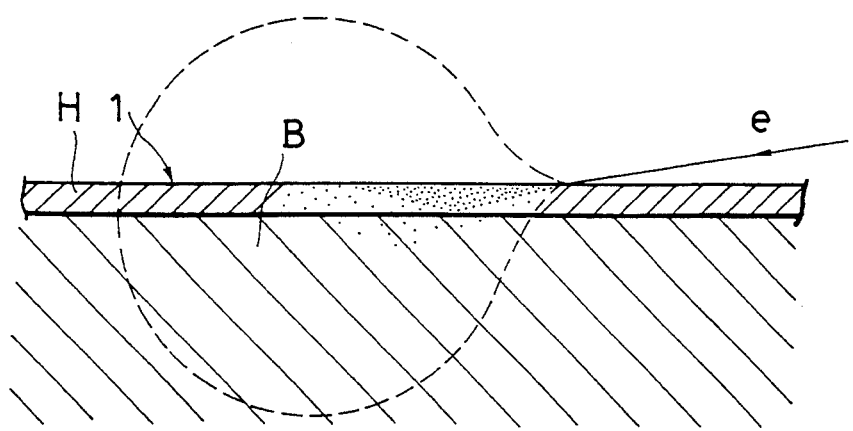
FIG. 13 is a cross sectional illustration showing a penetration of electron beam into a thin film of a sample in the apparatus of the first embodiment.

In addition, as shown in FIG. 13, because of the smaller incident angle of the electron beam, the conventionally encountered droplet-shaped penetration of the electron beam into the substrate member B of the sample 1 does not occur in this embodiment, and the X-ray fluorescence increases drastically at the take-off angle which is set to be equal to the total reflection angle of the characteristic X-rays. Thus, by detecting the emitted X-ray fluorescence at this predetermined take-off angle, it becomes possible to carry out the accurate X-ray fluorescence analysis of the components of the thin film H.

In this procedure, the inclination angle of the probe 30 of the energy dispersive X-ray detector 3 with respect to the sample 1, i.e., the take-off angle of the X-ray fluorescence (characteristic X-rays), can be adjusted as follows.

When the adjustment bolt 70 shown in FIG. 10 is turned, the tip end of the adjustment bolt 70 pushes the side face of the slide base 63, such that the slide base 63 slides along the guide rails 62. Here, the probe 30 of the energy dispersive X-ray detector 3 is supported with respect to the slide base 63 on the support frame 77, so that the energy dispersive X-ray detector 3 inclines along with the slide base 63, so as to change the inclination angle of the probe 30. It is preferable to set the take-off angle of the X-ray fluorescence (characteristic X-rays) to be not greater than 4 degrees in this embodiment.

Also, the height of the energy dispersive X-ray detector 3 can be adjusted by activating the expansion lift mechanism 82 by turning the adjustment bolt 84 shown in FIG. 12.

It is to be noted here that the complicated mechanism for supporting the energy dispersive X-ray detector 3 as described above in conjunction with FIG. 10 to FIG. 12 is required in this embodiment partly because the energy dispersive X-ray detector 3 as a whole is quite heavy as it includes the tank 29 containing the liquid nitrogen for cooling but is also quite expensive as it includes the probe 30 with a complicated structure, so that it is important to prevent time damaging of the energy dispersive X-ray detector, and partly because of the need for setting the inclination angle of the probe 30 accurately.

In this embodiment, because the connection room 79 formed by the space 78 formed between an inner wall of the protection tube 71 and an outer wall of the probe 30 and the spare room 32 is put in the vacuum state by means of the vacuum pump 33, the characteristic X-rays emitted from the sample surface enter the semiconductor X-ray detector 8 in the probe 30 through the vacuum region and the window sections 34 and 75 formed by beryllium or organic thin film, so that the absorption of the characteristic X-rays by the intermediate medium can be suppressed to the minimum amount.

Consequently, it becomes possible to detect the characteristic X-rays of time elements such as C, N, O, F, Na, Mg, and Al which can only be analyzed by using the characteristic X-rays with the energy below 1.7 KeV.

As for the elements having larger atomic number than those enumerated above, these elements not only emit $K\alpha$ lines, but also emit $K\beta$ lines, $L\alpha$ lines, $L\beta$ lines, and possibly $L\gamma$ lines and M lines as well, so that the appropriate one of time characteristic X-rays may be utilized in carrying out the X-ray Fluorescence analysis.

Figure 14:
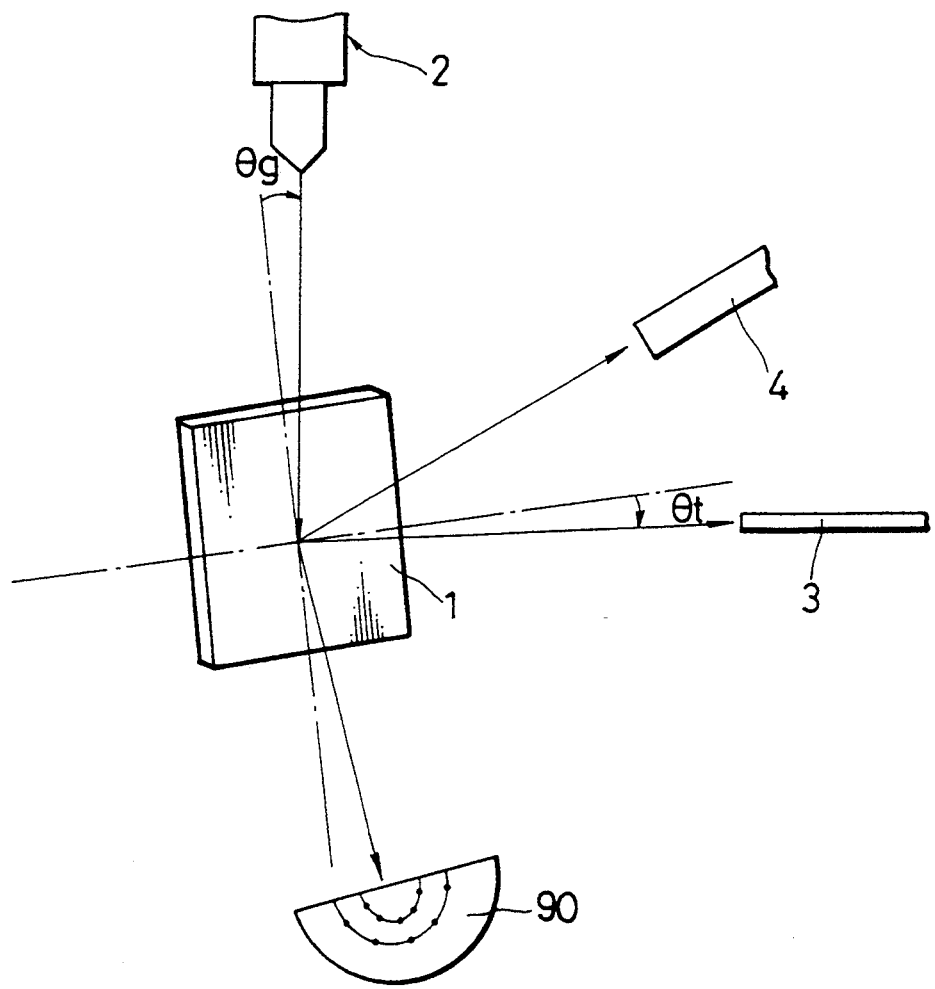
FIG. 14 is a schematic diagram indicating a conceptual configuration of a second embodiment of an apparatus for solid surface analysis according to the present invention.

Referring now to FIG. 14, a second embodiment of an apparatus for solid surface analysis according to the present invention will be described in detail.

As shown in FIG. 14, this second embodiment is a modification of the first embodiment described above which differs from the first embodiment by the additional inclusion of a fluorescent plate 90.

This fluorescent plate 90 is utilized in recording the diffraction pattern of the reflection high energy electrons which is caused by the fact that a part of the electrons from the electron gun 2 incident onto the sample 1 is diffracted at the sample surface. Such a diffraction pattern can be utilized in analyzing the crystalline structure of the sample surface.

Thus, in this second embodiment, it becomes possible to obtain an enlarged image of the sample surface according to the secondary electrons detected by the electron detector 4, and to obtain a diffraction pattern according to the reflection high energy electrons by using the fluorescent plate 90, while carrying out the X-ray fluorescence analysis of the sample surface according to the characteristic X-rays detected by the energy dispersive X-ray detector 3.

It is noted that the fluorescent plate 90 can easily be attached to the vacuum chamber 20 by using the auxiliary port 52 shown in FIG. 6 and FIG. 7 described above.

Now, the results of the experimental tests conducted by using the apparatus of the first embodiment described above will be described.

TEST 1

Using the apparatus of the first embodiment described above, the solid surface analysis of the sample having an oxide superconductor thin film with a composition of $YBa_2Cu_3O_x$ and a thickness of 800 Å formed on (100) plane of the MgO substrate was carried out. This oxide superconductor thin film was determined to have the composition of Y:Ba:Cu=1:1.9:2.8 from the composition analysis data obtained by the separately conducted inductively coupled plasma emission spectrometry.

After the internal pressure of the vacuum chamber 20 was set to be $1 \times 10^{-7}$ Torr, the electron beams having the energy of 20 KeV was irradiated onto the sample surface at three different settings of the incident angles $\theta g$ at 4°, 11°, and 90°, and the detection by the energy dispersive X-ray detector was carried out at three different settings of the take-off angle $\theta t$ at below 4°, 5° to 8°, and 10° to 13°, respectively.

Figure 15:
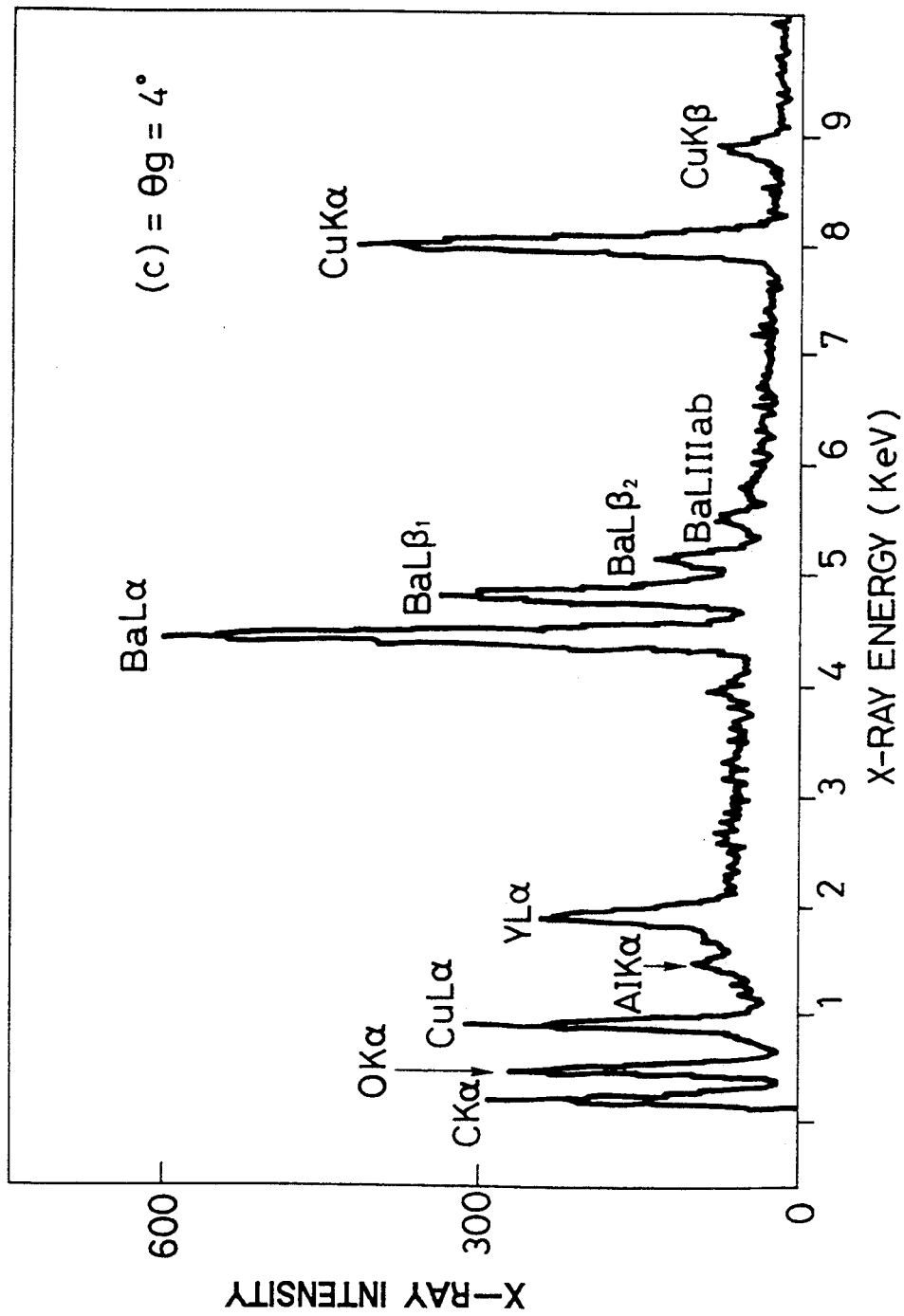
FIG. 15 is a graph of X-ray intensity versus X-ray energy indicating one result of the first experimental test using the apparatus of the first embodiment.
Figure 16:
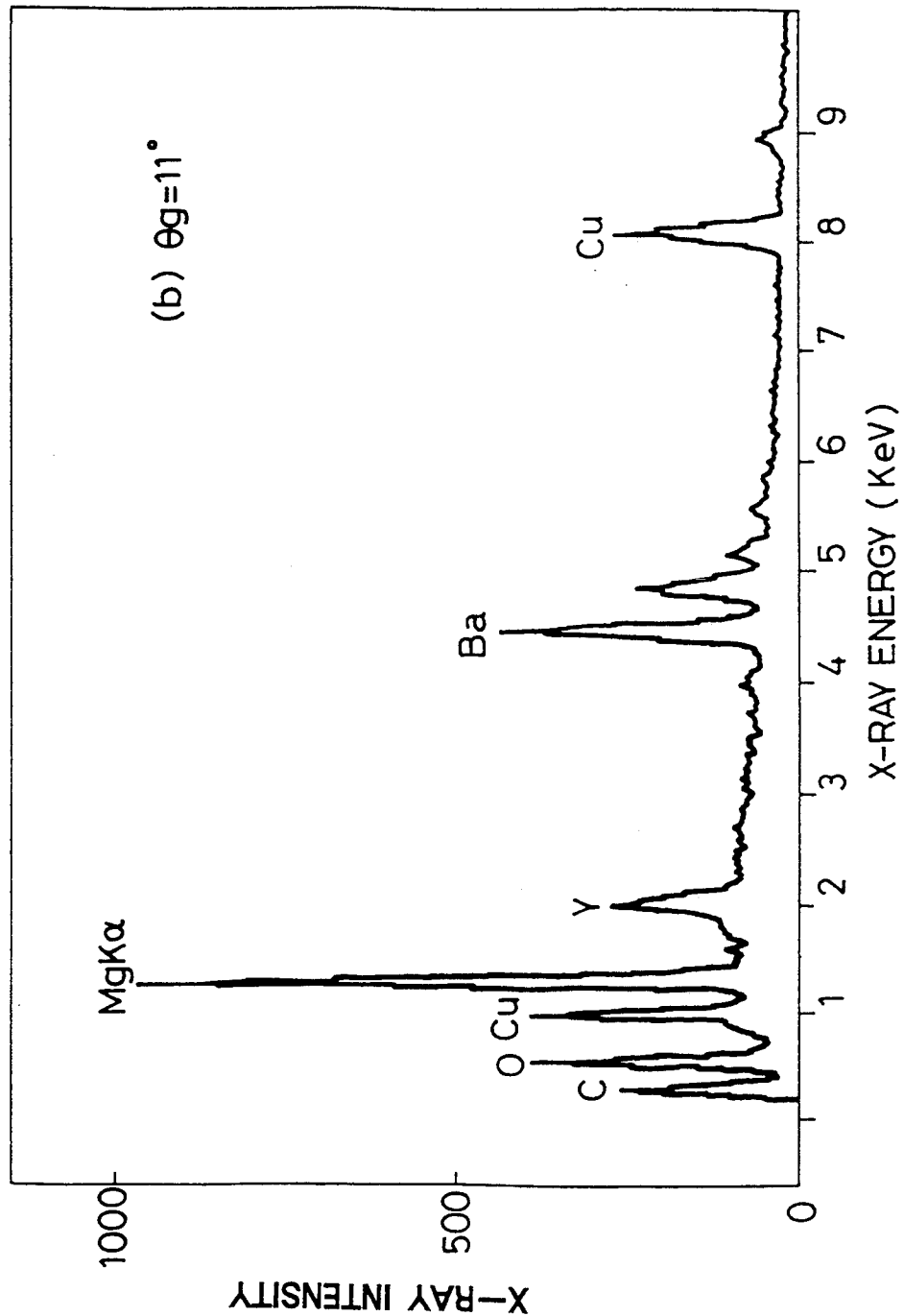
FIG. 16 is a graph of X-ray intensity versus X-ray energy indicating another result of the first experimental test using the apparatus of the first embodiment.
Figure 17:
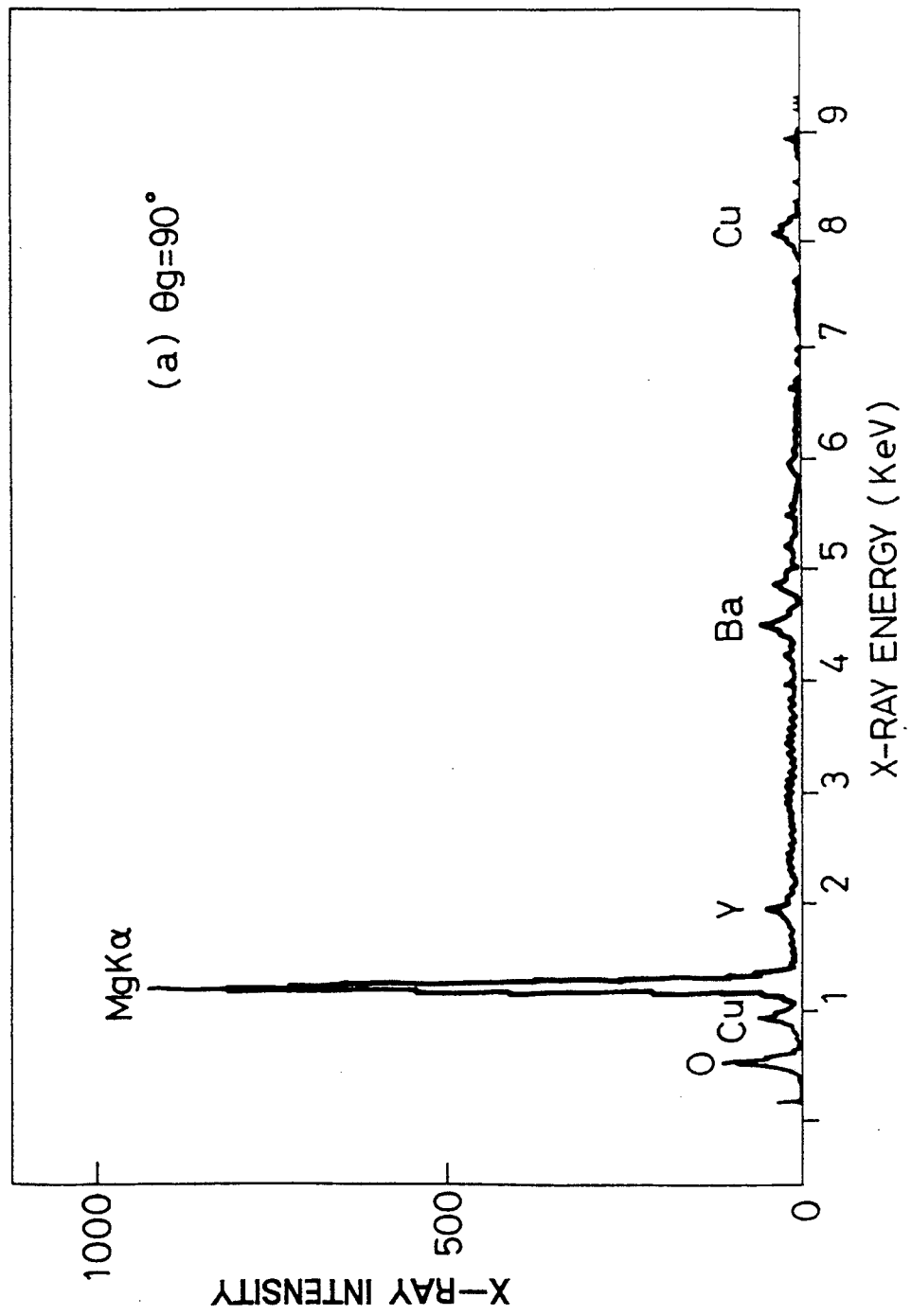
FIG. 17 is a graph of X-ray intensity versus X-ray energy indicating another result of the first experimental test using the apparatus of the first embodiment.

The results obtained by these experimental tests are shown in FIG. 15 to FIG. 17.

In a case of $\theta g=4°$ shown in FIG. 15, the Mg K$\alpha$ lines emitted from the MgO substrate were not observed at all and only the characteristic X-rays from YBa$_2$Cu$_3$O$_x$ thin film were observed. In other words, the characteristic X-rays of the constituent elements of the superconducting thin film alone are captured very clearly without the characteristic X-rays of the substrate. This fact itself is quite significant because there has been no report of such a result in the field of the oxide superconducting thin film analysis.

In FIG. 15, the detected Al K$\alpha$ lines are considered to be the characteristic X-rays of the sample holder 22 made of aluminum, and the detected C K$\alpha$ lines are considered to be the characteristic X-rays of the carbon tapes used in fixing the sample 1 to the sample holder 22.

In the result shown in FIG. 15, it is possible to make the accurate composition analysis of the thin film.

In this experimental test, it was also possible to obtain the enlarged image of the sample surface similar to that obtained by the conventional scanning electron microscope, by detecting the secondary electrons.

In a case of $\theta g=11°$ shown in FIG. 16, the Mg K$\alpha$ lines from the MgO substrate were observed to some extent, as the penetration of the electrons into the MgO substrate had occurred to some extent, but the characteristic X-rays emitted from YBa$_2$Cu$_3$O$_x$ thin film were also observed to be clearly identifiable in intensity, so that there is no serious trouble for making the accurate composition analysis of the thin film.

In a case of $\theta g=90°$ shown in FIG. 16, the Mg K$\alpha$ lines from the MgO substrate were observed to be very strong in intensity, and the characteristic X-rays from YBa$_2$Cu$_3$O$_x$ thin film were observed to be very weak in intensity, so that it is practically impossible to make the accurate composition analysis of the thin film.

From these results, it can be concluded that the incident angle of the electron beam should be in a range of not greater than 11 degrees. On the other hand, the incident angle for which time penetration of the electrons into the sample can be suppressed to the level of several thousand Å (which is approximately equal to the thickness of the thin film formed on the sample surface) is limited to be not greater than 15 degrees, so that it is preferable to set the incident angle to be not greater than 15 degrees at least.

TEST 2

Using the apparatus of the first embodiment described above, the solid surface analysis of the sample having an Au thin film with a thickness of 50 Å formed on (100) plane of the Si substrate was carried out in a manner substantially similar to that of the TEST 1 described above. Here, however, the incident angle $\theta g$ was set to be 4 degrees, while the take-off angle $\theta t$ was set to be three different settings of 0° to 3°, 5° to 8°, and 10° to 13°. The results obtained by these experimental tests are shown in FIG. 18.

Figure 18:
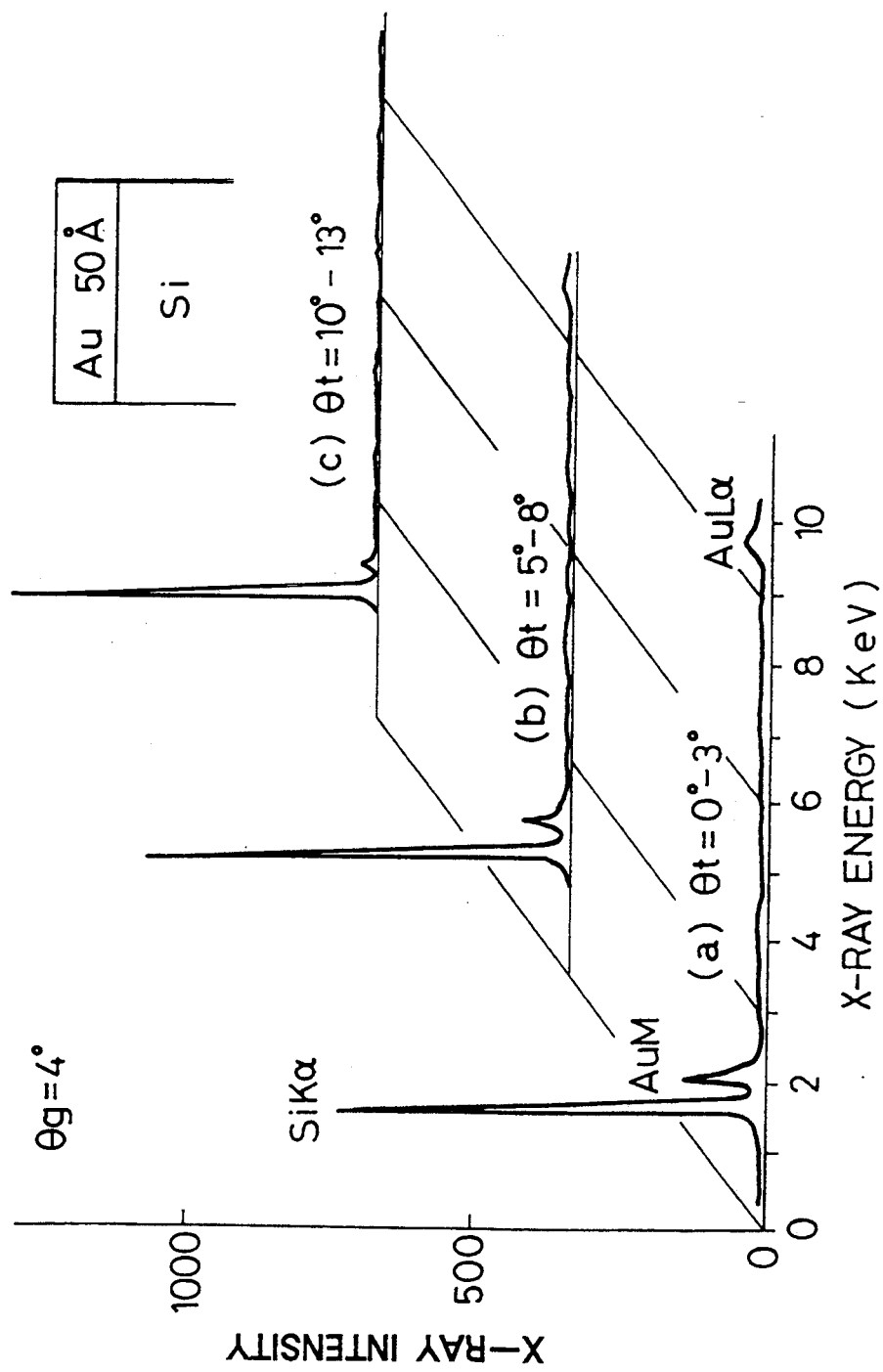
FIG. 18 is a graph of X-ray intensity versus X-ray energy indicating one result of the second experimental test using the apparatus of the first embodiment.

As can be seen in FIG. 18, the Au M lines of the characteristic X-rays of the Au thin film had the largest relative intensity with respect to the intensity of the Si K$\alpha$ lines when the take-off angle $\theta t$ was set to be 0° to 3° which is in a vicinity of the total reflection angle $\theta c$ (AuM-Si)=0.81°.

Also, using the apparatus of the first embodiment described above, the solid surface analysis of the sample having an Au thin film with a thickness of 125 Å formed on (100) plane of the Si substrate was carried out in a manner substantially similar to that of the TEST 1 described above. Here, however, the incident angle $\theta g$ was set to be 4 degrees, while the take-off angle $\theta t$ was set to be three different settings of 0° to 3°, 5° to 8°, and 10° to 13°. The results obtained by these experimental tests are shown in FIG. 19.

Figure 19:
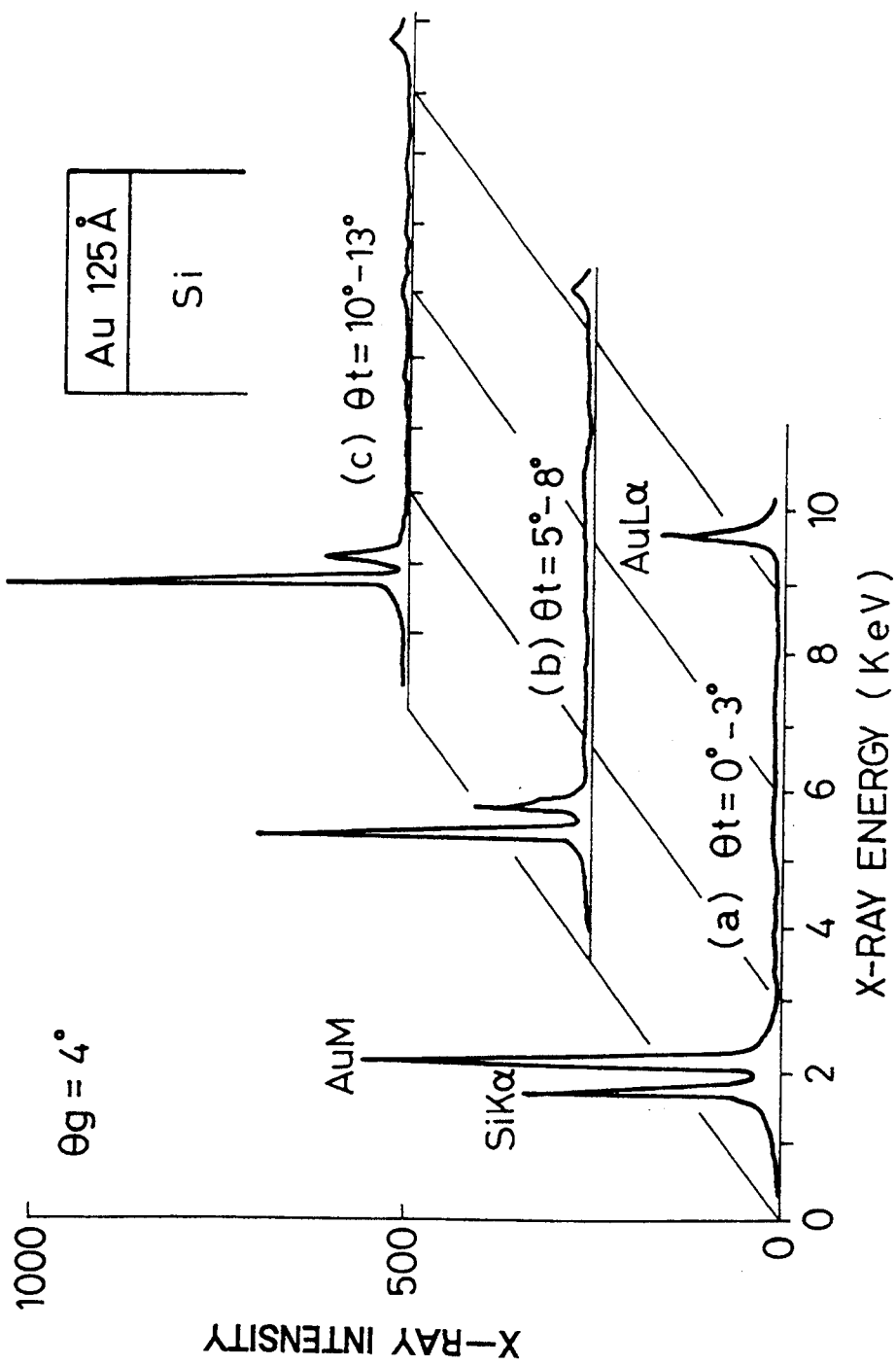
FIG. 19 is a graph of X-ray intensity versus X-ray energy indicating another result of the second experimental test using the apparatus of the first embodiment.

In this case, as can be seen in FIG. 19, the Au M lines of the characteristic X-rays of the Au thin film had the larger intensity than the intensity of the Si K$\alpha$ lines when the take-off angle $\theta t$ was set to be 0° to 3° which is in a vicinity of the total reflection angle $\theta c$ (AuM-Si)=0.81°.

It can be concluded from the results shown in FIG. 18 and FIG. 19 that the characteristic X-rays of the thin film at the similar intensity level as the characteristic X-rays of the substrate can be detected for the thin film of the thickness at the level of one hundred Å.

TEST 3

Using the apparatus of the first embodiment described above, the X-ray fluorescence analysis of the sample having an Mg thin film with a thickness of 10 Å formed on the Si substrate by the vacuum evaporation was carried out for a case of having the connection room 79 put in the vacuum state and a case of having the connection room 79 opened to the air.

After the internal pressure of the vacuum chamber 20 was set to be $1\times10^{-7}$ Torr, the electron beam having the energy of 20 KeV was irradiated onto the sample surface at the incident angle $\theta g$ equal to 4°, and the detection by the energy dispersive X-ray detector was carried out at the take-off angle $\theta t$ at below 4°.

Figure 20A:
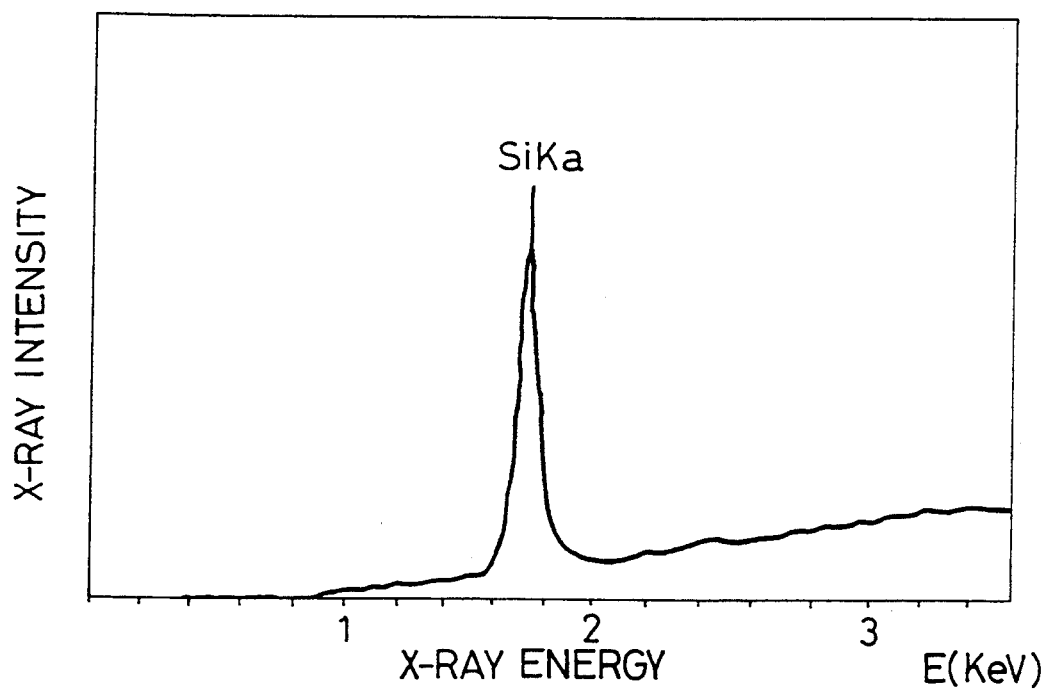
FIG. 20A is a graph of X-ray intensity versus X-ray energy indicating one result of the third experimental test using the apparatus of the first embodiment.
Figure 20B:
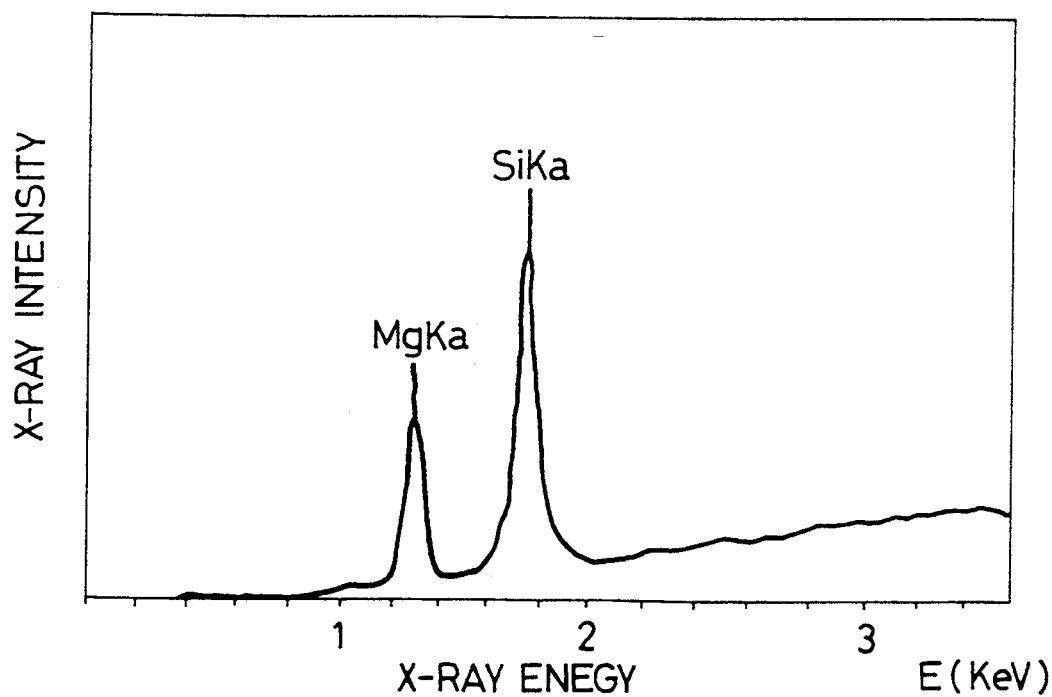
FIG. 20B is a graph of X-ray intensity versus X-ray energy indicating another result of the third experimental test for the apparatus of the first embodiment.

The results obtained by these experimental tests are shown in FIG. 20A and FIG. 20B, where FIG. 20A shows a case of having the connection room 79 opened to the air (with the air layer present between the vacuum chamber 20 and the probe 30), and FIG. 20B shows a case of having the connection room 79 put in the vacuum state (without the air layer between vacuum chamber 20 and the probe 30).

In a case of FIG. 20B, it was possible to clearly detect the K$\alpha$ lines of Mg having the energy of 1.253 KeV, so that it was possible to detect the presence of the Mg thin film on the sample surface.

In contrast, in a case of FIG. 20A, it was not possible to detect the presence of Mg thin film on the sample surface.

As described above, according to the first embodiment described above, the X-ray fluorescence analysis of the sample surface using the X-ray fluorescence and the enlarged image of the sample surface using the secondary electrons can be obtained simultaneously by detecting the X-ray fluorescence and the secondary electrons emitted from the sample surface excited by the electron beam from the electron gun at the energy dispersive X-ray detector and the electron detector, respectively.

As a result, it becomes possible in the apparatus of this first embodiment to carry out the hereto unavailable manner of making the X-ray fluorescence analysis while viewing the enlarged image of the sample surface.

Moreover, a large amount of the characteristic X-rays are detected at the take-off angle not greater than 4 degrees which is in a vicinity of the total reflection angle of the X-rays so that it is possible to carry out the accurate analysis. In addition, by shooting the electron beam at the incident angle not greater than 4 degrees, it becomes possible to detect the characteristic X-rays and the secondary electrons due to the surface portion alone without causing the penetration of the electrons into the substrate portion, so that it is possible to carry out the accurate analysis of the thin surface portion.

Furthermore, by additionally incorporating the fluorescent plate as in the second embodiment described above, it becomes possible to obtain an enlarged image of the sample surface according to the secondary electrons detected by the electron detector, and to obtain a diffraction pattern according to the reflection high energy electrons by using the fluorescent plate, while carrying out the X-ray fluorescence analysis of the sample surface according to the characteristic X-rays detected by the energy dispersive X-ray detector, so that the comprehensive analysis of the sample using three different data of the enlarged image, diffraction pattern, and X-ray fluorescence can be made.

In addition, the energy dispersive X-ray detector can be used without the intervening air layer between the probe and the sample as the energy dispersive X-ray detector is detachably attached to the vacuum chamber through the connecting room which can be put in the vacuum state, so that the characteristic X-rays having the energy below 1.7 KeV can be detected without the absorption or dissipation due to the intermediate medium. Consequently, it becomes possible to detect the characteristic X-rays of the elements such as C, N, O, F, Na, Mg, and Al which can only be analyzed by using the characteristic X-rays with the energy below 1.7 KeV.

Moreover, the energy dispersive X-ray detector can be detached from the vacuum chamber by releasing the vacuum state of the connecting room alone, without releasing the vacuum state of the vacuum chamber itself, so that the expensive energy dispersive X-ray detector can be easily shared among a plurality of vacuum chambers.

It is to be noted here that the electron beam used in the first and second embodiment described above is only an example of the energy particles, and can be replaced by the other high energy particles capable of exciting the sample surface to generate the X-ray fluorescence (characteristic X-rays) such as X-rays.

Referring now to FIG. 21 to FIG. 24, a third embodiment of an apparatus for solid surface analysis according to the present invention will be described in detail. In the following, those parts of this third embodiment which are substantially equivalent to the corresponding parts of the first embodiment described above will be given the same reference numerals in the figures and their description will be omitted.

Figure 21:
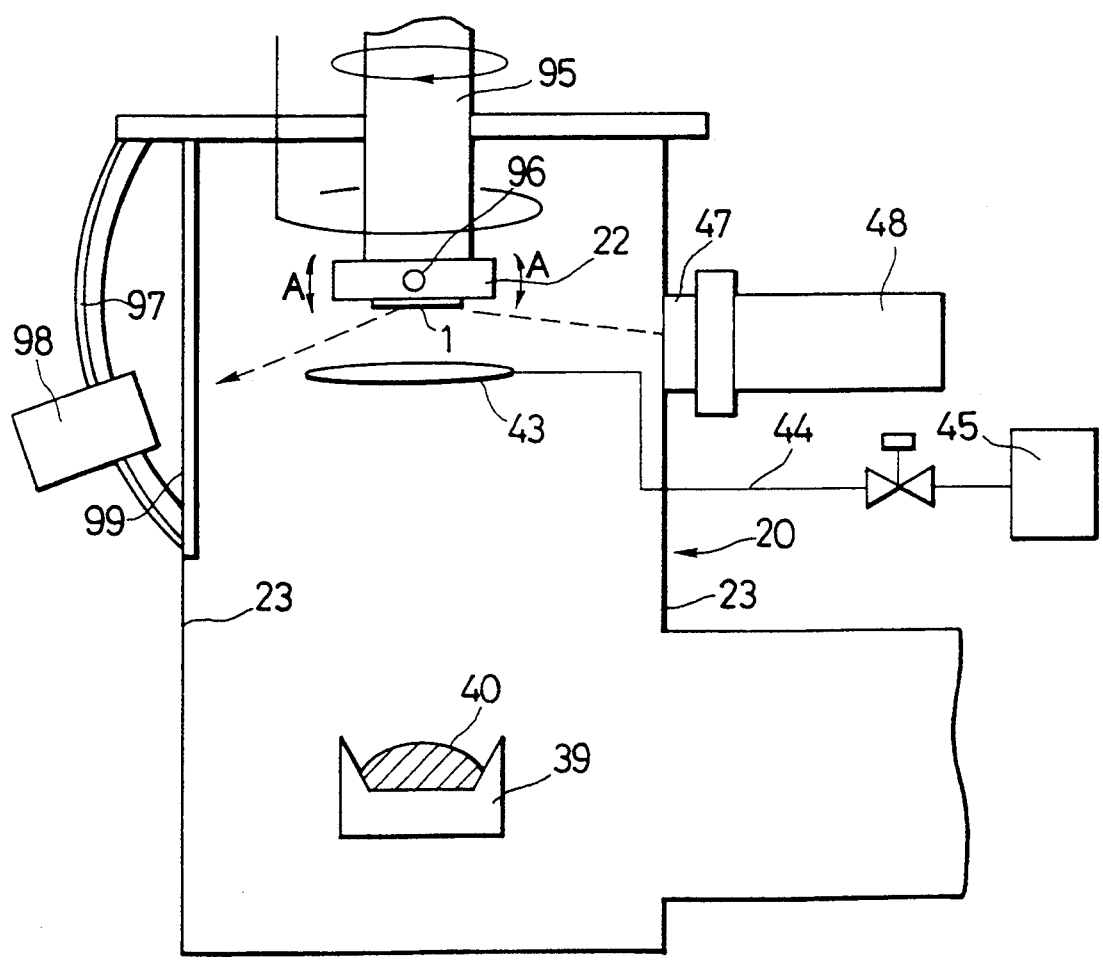
FIG. 21 is a schematic longitudinal cross sectional view of a vacuum chamber in a third embodiment of an apparatus for solid surface analysis according to the present invention.

As shown in FIG. 21, in this third embodiment, the sample holder 22 is freely rotatably attached to a cylinder member 95 provided through the ceiling of the vacuum chamber 20 by means of a support axis 96, such that the sample 1 mounted on the bottom face of the sample holder 22 can be rotated in a direction of the arrow A by a rotational driving mechanism (not shown) including gears and a motor provided inside the cylinder member 95. In other words, in this third embodiment, the sample 1 can be rotated in a direction for inclining the sample 1 at a desired angle.

Also, the vacuum chamber 20 is equipped with a sample exchange room (not shown) which can be put in the vacuum state, such that the sample can be mounted on the bottom face of the sample holder 22 without breaking the vacuum state of the vacuum chamber 20 by using the sample carrier mechanism (not shown) through a gate valve provided in the sample exchange room.

Figure 22:
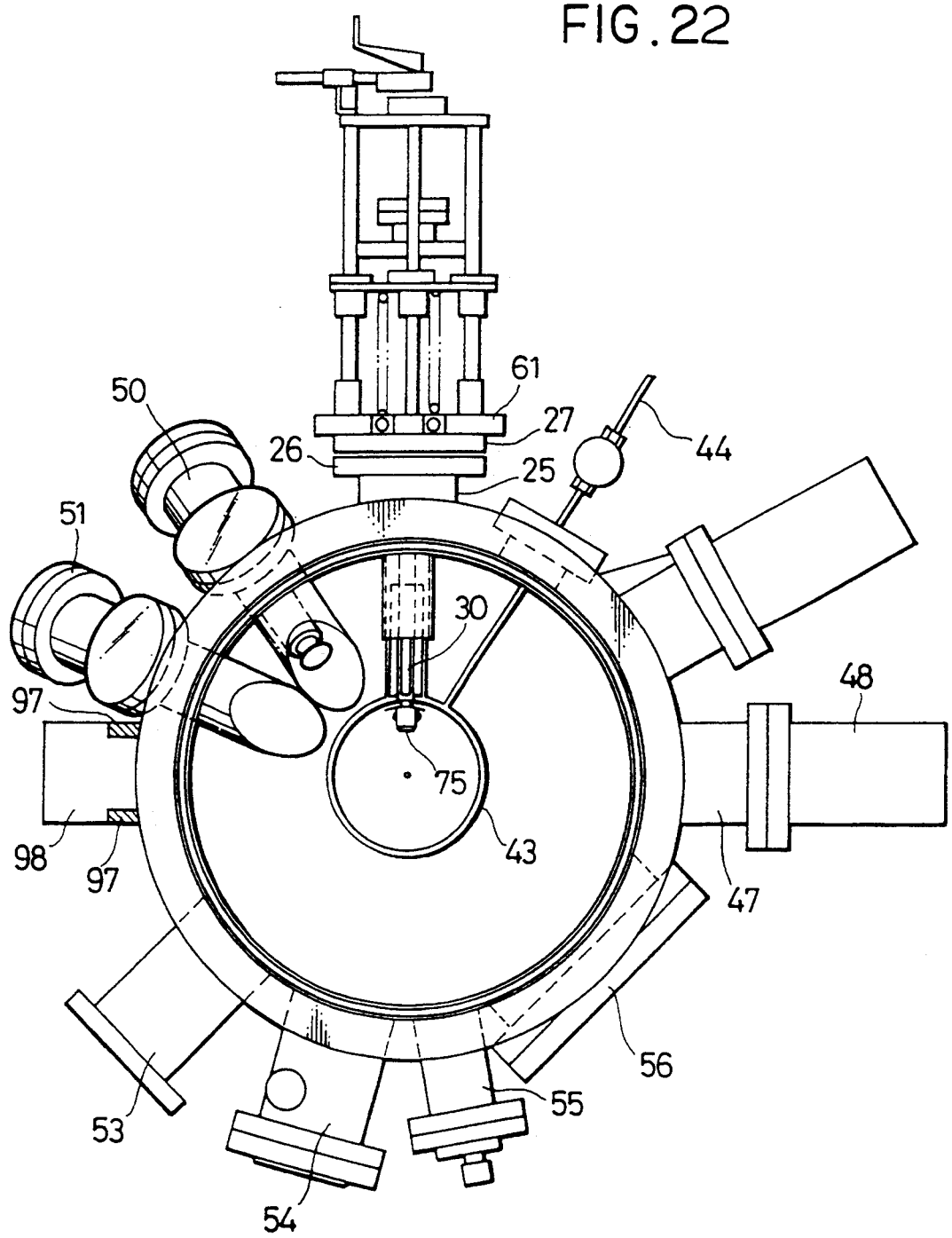
FIG. 22 is a transverse cross sectional view of the apparatus of the third embodiment.

In addition, as shown in FIG. 21 and FIG. 22, on an outer side of the vacuum chamber 20, there is provided a pair of arc shaped rail members 97 stretching in the vertical direction in a shape of a circle centered around the sample 1 mounted on the sample holder 22, and a diffracted X-ray detector 98 is mounted on the rail members 97 to be freely movable in the vertical direction along the circle centered around the sample 1 traced by the rail members 97.

Moreover, a part of the side wall 23 of the vacuum chamber 20 which is facing against the rail members 97 is formed by a vertically elongated window 99 made of high X-ray transmission material such as beryllium.

Also, as shown in FIG. 21 and FIG. 22, in this third embodiment, an X-ray generation device 48 is used in place of the electron gun in the first embodiment described above. This X-ray generation device 48 is formed by a wellknown X-ray source such as an X-ray tube.

Here, because it is necessary to carry out the X-ray analysis of various elements, the X-ray generation device 48 is required to be capable of generating the high energy X-rays. For example, when the X-rays having the energy of 8.04 such as Cu Kα lines KeV are used for irradiating the sample, the X-rays with the energy higher than that cannot be obtained from the sample, so that it is inconvenient for obtaining the characteristic X-rays such as Kα lines, Kβ lines, Lα lines, Lβ lines, and M lines for various elements. For this reason, it is preferable in this third embodiment to use the X-rays with the energy approximately equal to 22 KeV such as the Kα lines of Ag.

Figure 23:
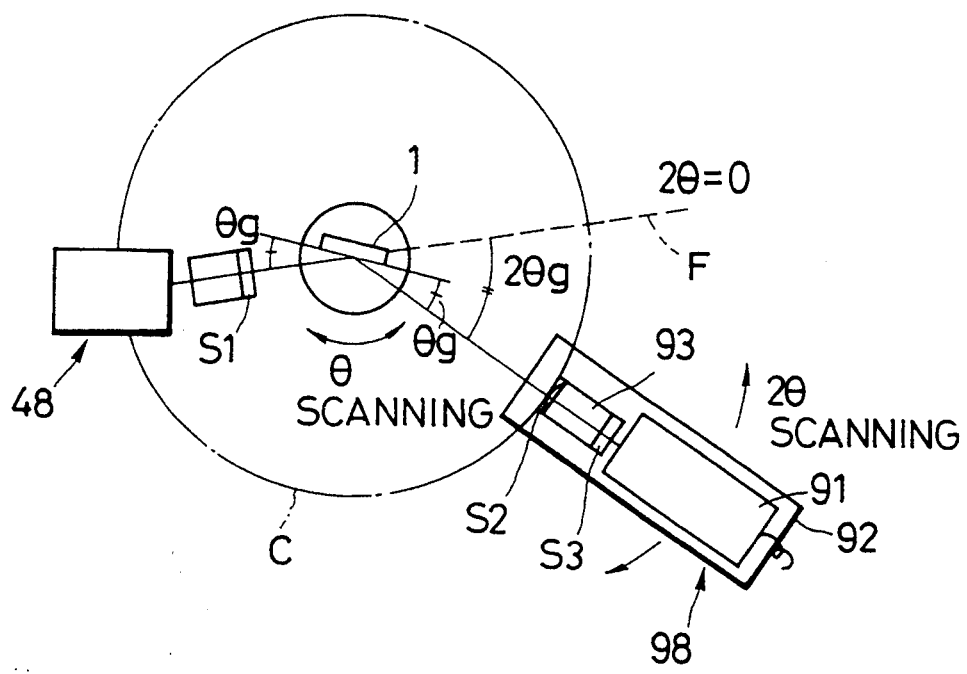
FIG. 23 is a schematic diagram showing a configuration of major components in the apparatus of the third embodiment in further detail.

Also, as shown in FIG. 23, the X-ray generation device 48 is equipped with a slit S1 attached at its tip end, while the diffracted X-ray detector 98 comprises a pick up unit 93 including a couple of slits S2 and S3, and a counter unit 91 including an X-ray counter connected to the pick up unit 93, both of which are integrally mounted on a counter frame 92 which is slidable along the rail members 97.

Figure 24:
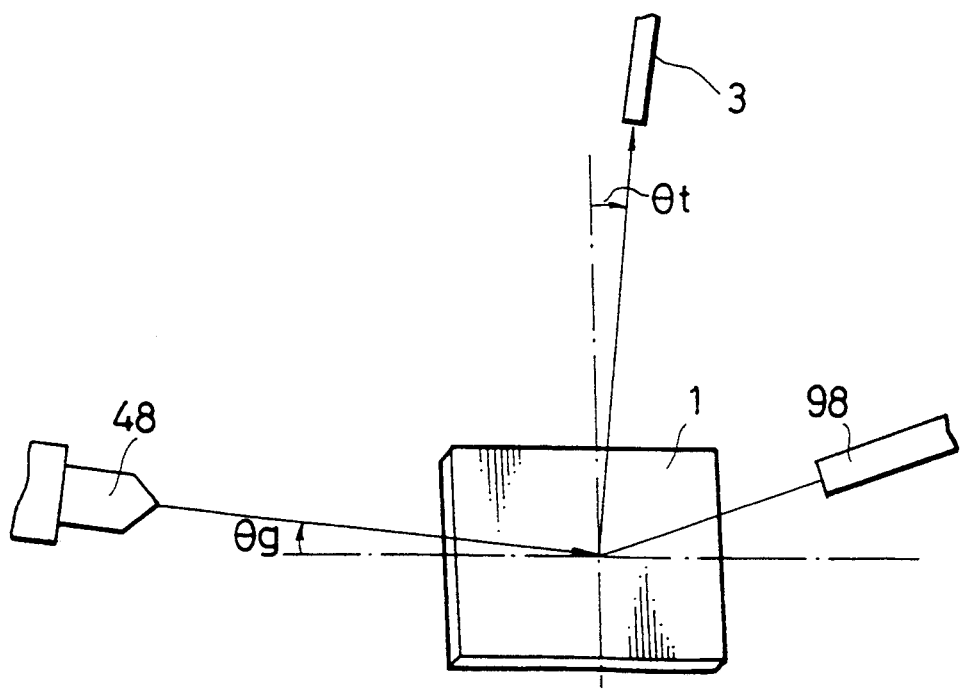
FIG. 24 is a schematic diagram indicating a conceptual configuration of a third embodiment of an apparatus for solid surface analysis according to the present invention.

As shown in FIG. 24, the apparatus of this third embodiment essentially includes the X-ray generation device 48 for irradiating the X-rays focused by the slit S1 at a predetermined incident angle $\theta g$ onto a surface of a substrate shaped sample 1 on which a film to be analyzed is formed, the energy dispersive X-ray detector 3 for detecting X-ray fluorescence (characteristic X-rays) emitted from the surface of the sample 1 excited by the X-rays from the X-ray generation device 48 at a predetermined take-off angle $\theta t$, and the diffracted X-ray detector 98 for detecting the X-rays diffracted by the surface of the sample 1 excited by the X-rays from the X-ray generation device 48 while being moved along the circle C shown in FIG. 23, which is centered around the sample 1 and traced by the rail members 97, in synchronization to the rotation of the sample 1.

Here, the inclination angle of the probe 30 of the energy dispersive X-ray detector 3 can also be changed easily as the probe 30 inserted into the protection tube 71 can be inclined by the movement of the slide base 63, as the bellows section of the probe casing 35 easily allows the change of the orientation of the tip end of the protection tube 71.

In this third embodiment, for the elements having larger atomic number than those of C, N, O, F, Na, Mg, and Al, because such elements not only emit Kα lines, but also emit Kβ lines, Lα lines, Lβ lines, and possibly Lγ lines and M lines as well, so that the appropriate one of the characteristic X-rays may be utilized in carrying out the X-ray fluorescence analysis. More specifically, the Kα lines can be detected for the elements with the atomic number below 17 (such as Al, Mg, Na, Ne, F, O, and N), while the Kβ lines can be detected for the elements with the atomic number between 20 and 37 (Ca to Rb), and the M lines can be detected for the elements with the atomic number between 41 to 70 (Nb to Ta), so that these elements contained in the sample can be identified by observing these characteristic X-rays, Now, the X-ray diffraction analysis operation of this apparatus of the third embodiment will be described in detail.

In carrying out the X-ray diffraction analysis, first, the X-rays (Ag Kα lines) generated by the X-ray generation device 48 are irradiated onto the sample 1 at the predetermined incident angle $\theta g$. Next, the diffracted X-ray detector 98 is moved in the vertical direction along the rail members 97 such that the take-off angle of the diffracted X-rays takes a value equal to $2\theta g$ with respect to the incident direction F of the incident X-rays, as shown in FIG. 23. Then, the sample 1 and the diffracted X-ray detector 98 are rotated for the prescribed angle simultaneously by maintaining this angle relationship of $\theta g$ and $2\theta g$ described above, which is achieved by synchronizing the rotation of the sample holder 22 and the rotation of the diffracted X-ray detector 98.

Here, it is to be noted that the diffraction angle satisfying the diffraction condition may be displaced according to the wavelength of the X-rays used, so that the angle relationship of $\theta g$ and $2\theta g$ described above may need to be adjusted according to the wavelength of the X-rays used.

By detecting the diffracted X-rays at the diffracted X-ray detector 98 in this manner, it is possible to obtain the diffraction pattern having the diffraction peak at the counter unit 91, so that the X-ray diffraction analysis can be carried out according to the obtained diffraction peak. Here, because the diffraction peak is obtained from the X-rays emitted from the very thin surface portion of the sample 1, so that it becomes possible to identify the components of the thin film formed on the sample surface from this X-ray diffraction analysis.

Now, the results of the experimental tests conducted by using the apparatus of the third embodiment described above will be described.

TEST 4

Using the apparatus of the third embodiment described above, the X-ray fluorescence analysis of the sample having an oxide superconductor thin film with a composition of $YBa_2Cu_3O_x$ and a thickness of 0.2 μm formed on the MgO substrate was carried out for a case of having the connection room 79 put in the vacuum state and a case of having the connection room 79 opened to the air.

After the internal pressure of the vacuum chamber 20 was set to be $1 \times 10^{-7}$ Torr, the Ag Kα lines having the energy of 22 KeV were irradiated onto the sample surface at the incident angle $\theta g$ equal to 4°, and the detection by the energy dispersive X-ray detector was carried out at the take-off angle $\theta t$ at below 4°.

Figure 25A:
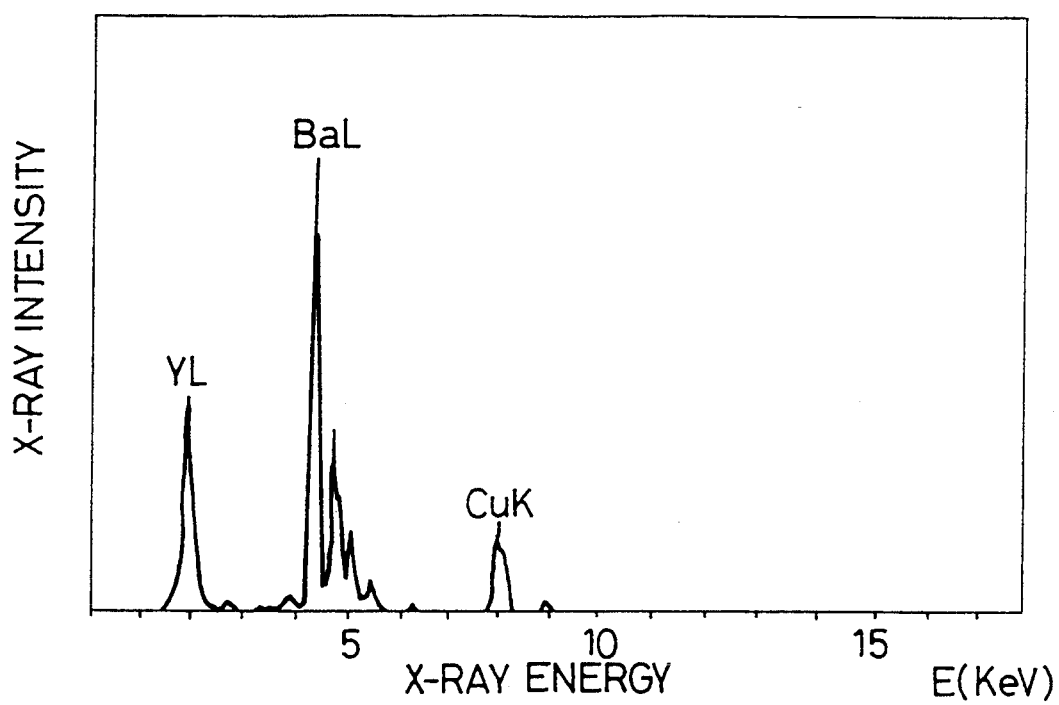
FIG. 25A is a graph of X-ray intensity versus X-ray energy indicating one result of the fourth experimental test using the apparatus of the third embodiment.
Figure 25B:
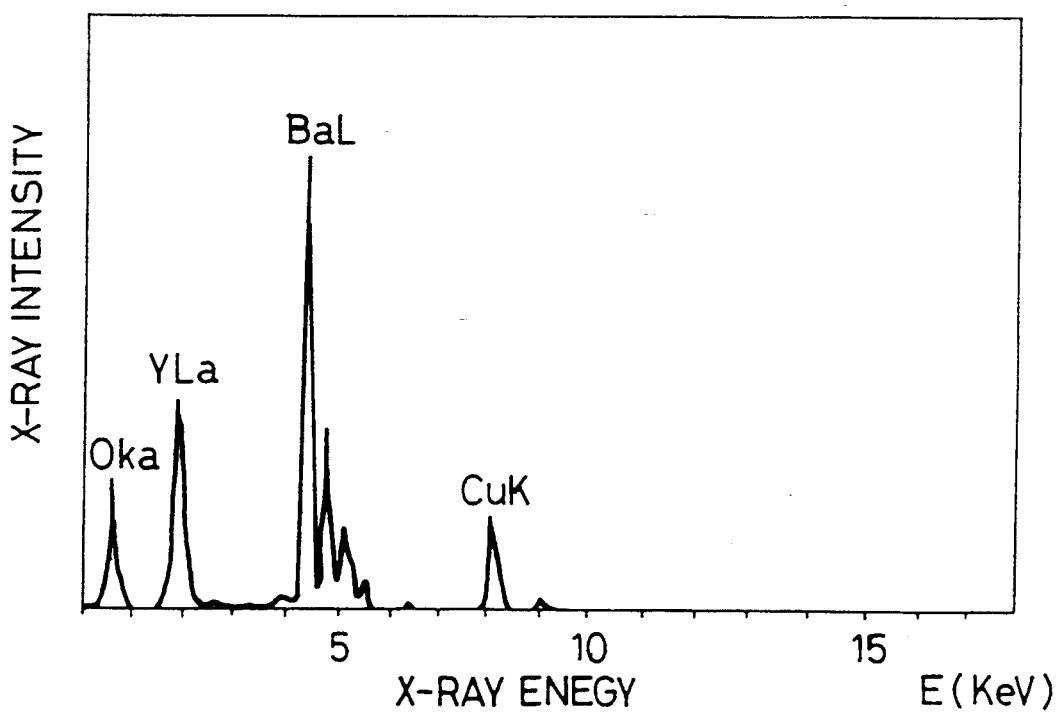
FIG. 25B is a graph of X-ray intensity versus X-ray energy indicating another result of the fourth experimental test for the apparatus of the third embodiment.

The results obtained by these experimental tests are shown in FIG. 25A and FIG. 25B, where FIG. 25A shows a case of having the connection room 79 opened to the air (with the air layer present between the vacuum chamber 20 and the probe 30), and FIG. 25B shows a case of having the connection room 79 put in the vacuum state (without the air layer between vacuum chamber 20 and the probe 30).

It was possible to clearly detect the presence of the $YBa_2Cu_3O_x$ thin film on the sample surface in a case of FIG. 25B. As can be seen by comparing FIG. 25A and FIG. 25B, in a case of FIG. 25A, it was not possible to detect the presence of Oxygen, whereas in a case of FIG. 25B, it was possible to detect the presence of Oxygen clearly. This result indicates that it was possible to satisfactorily detect the characteristic X-rays (Kα lines) of Oxygen which has the energy equal to 0.525 KeV which is below 1.7 KeV by making no air layer Present between the sample 1 and the probe 30.

TEST 5

Using the apparatus of the third embodiment described above, the X-ray diffraction analysis of the sample having an oxide superconductor thin film with a composition of $YBa_2Cu_3O_x$ and a thickness of 0.2 μm formed on the MgO substrate was carried out.

After the internal pressure of the vacuum chamber 20 was set to be $1 \times 10^{-7}$ Torr, the Ag Kα lines having the energy of 22 KeV were irradiated onto the sample surface at the incident angle $\theta g$, and the detection by the diffracted X-ray detector 98 was carried out at the take-off angle $\theta t$ equal to $2\theta g$ while the sample 1 and the diffracted X-ray detector 98 are synchronously rotated.

Figure 26:
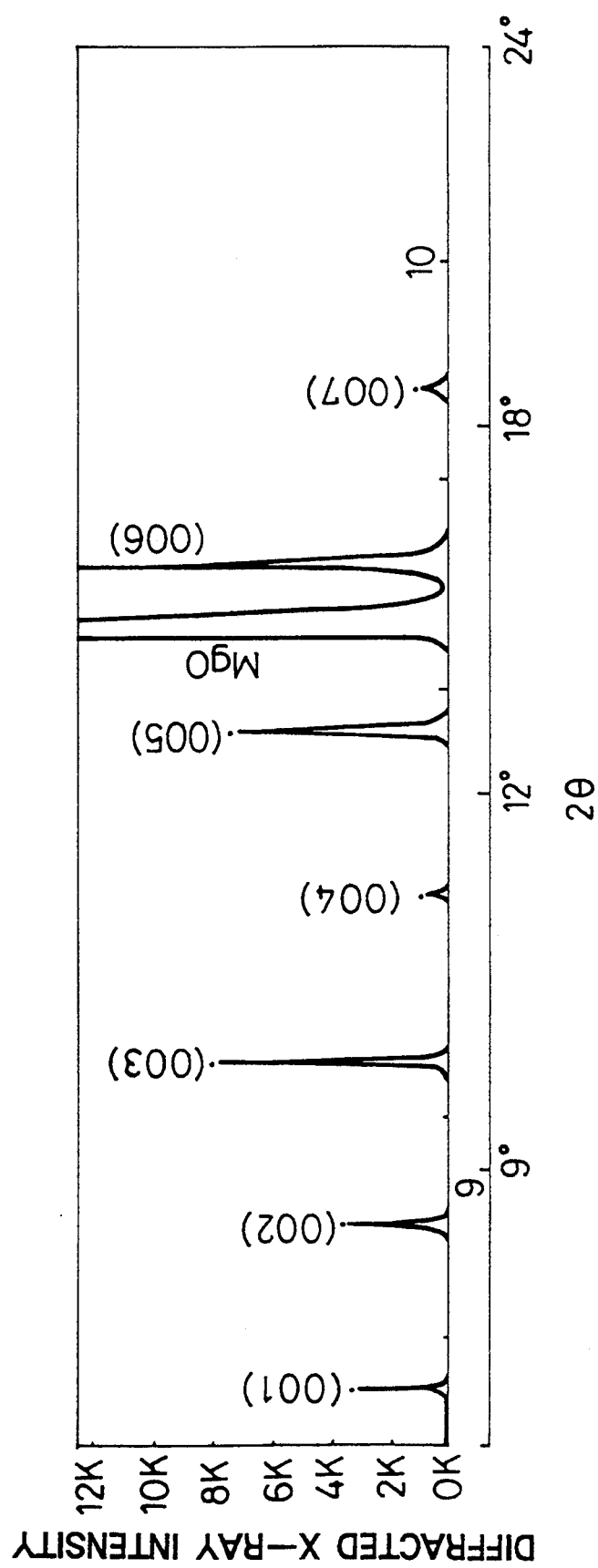
FIG. 26 is a graph of diffracted X-ray intensity versus scanning angle indicating one result of the fifth experimental test using the apparatus of the third embodiment.

The result obtained by this experimental test is shown in FIG. 26. As can be seen clearly in FIG. 26, it was possible to obtain the diffraction pattern for the MgO of the substrate as well as the diffraction patterns corresponding to all the lattice Planes of the oxide semiconductor thin film.

As described above, according to the third embodiment described above, a large amount of the characteristic X-rays are detected at the take-off angle not greater than 4 degrees which is in a vicinity of the total reflection angle of the X-rays so that it is possible to carry out the accurate analysis. In addition, by shooting the incident X-rays at the incident angle not greater than 4 degrees, it becomes possible to detect the characteristic X-rays from the surface portion alone, so that it is possible to carry out the accurate analysis of the thin surface portion.

Moreover, by detecting the diffracted X-rays by the diffracted X-ray detector provided in addition to the energy dispersive X-ray detector while the sample and the diffracted X-ray detector are synchronously rotated, it is possible to detect the diffraction peak, so that it is also possible to carry out the X-ray diffraction analysis in addition to the X-ray fluorescence analysis.

in addition, the energy dispersive X-ray detector can be used without the intervening air layer between the probe and the sample as the energy dispersive X-ray detector is detachably attached to the vacuum chamber through the connecting room which can be put in the vacuum state, so that the characteristic X-rays having the energy below 1.7 KeV can be detected without the absorption or dissipation due to the intermediate medium. Consequently, it becomes possible to detect the characteristic X-rays of the elements such as C, N, O, F, Na, Mg, and Al which can only be analyzed by using the characteristic X-rays with the energy below 1.7 KeV. Moreover, the Kα lines can be detected for the elements with the atomic number below 17 (such as Al, Mg, Na, Ne, F, O, and N), while the K$\beta$ lines can be detected for the elements with the atomic number between 20 and 37 (Ca to Rb), and the M lines can be detected for the elements with the atomic number between 41 to 70 (Nb to Ta), so that these elements contained in the sample can be identified by observing these characteristic X-rays.

Furthermore, the energy dispersive X-ray detector can be detached from the vacuum chamber by releasing the vacuum state of the connecting room alone, without releasing the vacuum state of the vacuum chamber itself, so that the expensive energy dispersive X-ray detector can be easily shared among a plurality of vacuum chambers.

It is to be noted that besides those already mentioned above, many modifications and variations of the above embodiments may be made without departing from the novel and advantageous features of the present invention. Accordingly, all such modifications and variations are intended to be included within the scope of the appended claims.

What is claimed is:

1. An apparatus for solid surface analysis, comprising:
   a vacuum chamber means for containing a sample to be analyzed;
   electron gun means for irradiating an electron beam onto a surface of the sample contained in the vacuum chamber means;
   energy dispersive X-ray detector means for detecting X-ray fluorescence emitted from the surface of the sample excited by the electron beam from the electron gun means;
   electron detector means for detecting secondary electrons emitted from the surface of the sample excited by the electron beam from the electron gun means: and
   a connection means for connecting the energy dispersive X-ray detector means to the vacuum chamber means, having one end connected to the vacuum chamber means, another end capable of detachably attaching the energy dispersive X-ray detector means, and a vacuum pump for creating a vacuum state in an interior of the connection means without affecting a vacuum state inside the vacuum chamber means.

2. The apparatus of claim 1, wherein the energy dispersive X-ray detector means is positioned with respect to the sample such that the energy dispersive X-ray detector detects the X-ray fluorescence at a take-off angle in a vicinity of a total reflection angle of X-ray.

3. The apparatus of claim 1, further comprising a fluorescence plate means for recording a reflected high energy electron diffraction pattern for the electrons diffracted at the surface of the sample.

4. The apparatus of claim 1, wherein the electron gun means irradiates the electron beam at an incident angle riot greater than 15 degrees.

5. The apparatus of claim 4, wherein the electron gun means irradiate the electron beam at an incident angle not greater than 4 degrees.

6. The apparatus of claim 1, wherein the energy dispersive X-ray detector means detects the X-ray fluorescence at a take-off angle not greater than 4 degrees.

7. The apparatus of claim 1, wherein the electron gun means is a scanning electron microscope.

8. The apparatus of claim 1, further comprising means for adjusting an angle of the energy dispersive X-ray detector means with respect to the sample.

9. An apparatus for solid surface analysis, comprising:
   a vacuum chamber means for containing a sample to be analyzed;
   X-ray generation means for irradiating X-rays onto a surface of the sample contained in the vacuum chamber means;
   energy dispersive X-ray detector means for detecting X-ray fluorescence emitted from the surface of the sample excited by the X-rays from the X-ray generating means;
   diffracted X-ray detector means for detecting the X-rays diffracted by the surface of the sample excited by the X-rays from the X-ray generation means; and
   a connection means for connecting the energy dispersive X-ray detector means to the vacuum chamber means, having one end connected to the vacuum chamber means, another end capable of detachably attaching the energy dispersive X-ray detector means, and a vacuum pump for creating a vacuum state in an interior of the connection means without affecting a vacuum state inside the vacuum chamber means.

10. The apparatus of claim 9, wherein the energy dispersive X-ray detector means is positioned with respect to the sample such that the energy dispersive X-ray detector detects the X-ray fluorescence at a take-off angle in a vicinity of a total reflection angle of X-ray.

11. The apparatus of claim 9, further comprising means for rotating the sample in the vacuum chamber means and means for moving the diffracted X-ray detector means along a circle centered around the sample in the vacuum chamber means, wherein the diffracted X-ray detector means detects the diffracted X-rays while being moved along the circle centered around the sample in the vacuum chamber means synchronously with a rotation of the sample.

12. The apparatus of claim 9, wherein the X-ray generation means irradiates the X-rays having an energy not less than 22 KeV.

13. The apparatus of claim 9, wherein the X-ray generation means irradiates the X-rays at an incident angle not greater than 4 degrees.

14. The apparatus of claim 9, wherein the energy dispersive X-ray detector means detects the X-ray fluorescence at a take-off angle not greater than 4 degrees.

15. The apparatus of claim 9, further comprising means for adjusting an angle of the energy dispersive X-ray detector means with respect to the sample.

16. An apparatus for solid surface analysis, comprising:
   a vacuum chamber means for containing a sample to be analyzed;
   energy particle beam generation means for irradiating energy particle beam onto a surface of the sample contained in the vacuum chamber means;
   energy dispersive X-ray detector means for detecting X-ray fluorescence emitted from the surface of the sample excited by the energy particle beam from the energy particle beam generation means; and
   connection means for connecting the energy dispersive X-ray detector means to the vacuum chamber means, having one end connected to the vacuum chamber means, another end capable of detachably attaching the energy dispersive X-ray detector means, and a vacuum pump for putting an interior of the connection means in a vacuum state without affecting a vacuum state inside the vacuum chamber means.

17. The apparatus of claim 16, wherein the energy dispersive X-ray detector means is positioned with respect to the sample such that the energy dispersive X-ray detector detects the X-ray fluorescence at a take-off angle in a vicinity of a total reflection angle of X-ray.

18. The apparatus of claim 16, wherein the energy particle beam generation means irradiates the energy particle beam at an incident angle not greater than 4 degrees.

19. The apparatus of claim 16, wherein the energy dispersive X-ray detector means detects the X-ray fluorescence at a take-off angle not greater than 4 degrees.

20. The apparatus of claim 16, further comprising means for adjusting an angle of the energy dispersive X-ray detector means with respect to the sample.

* * * * *

UNITED STATES PATENT AND TRADEMARK OFFICE
CERTIFICATE OF CORRECTION

PATENT NO. : 5,369,275
DATED : November 29, 1994
INVENTOR(S) : Toshio USUI, et al.

It is certified that error appears in the above-indentified patent and that said Letters Patent is hereby corrected as shown below:

On the title page, Item [73], the third Assignee's city is spelled incorrectly. It should read:

--Kawasaki--

Signed and Sealed this

Fourth Day of April, 1995

Attest:

BRUCE LEHMAN

*Attesting Officer*  *Commissioner of Patents and Trademarks*